United States Patent
Buckhaults et al.

(10) Patent No.: US 8,029,764 B2
(45) Date of Patent: Oct. 4, 2011

(54) METHODS FOR DETECTION OF COLORECTAL CANCER

(75) Inventors: Phillip Buckhaults, Columbia, SC (US); Kenneth W. Kinzler, Baltimore, MD (US); Bert Vogelstein, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1529 days.

(21) Appl. No.: 10/487,934

(22) PCT Filed: Sep. 9, 2002

(86) PCT No.: PCT/US02/28518
§ 371 (c)(1),
(2), (4) Date: Aug. 23, 2004

(87) PCT Pub. No.: WO03/022863
PCT Pub. Date: May 3, 2003

(65) Prior Publication Data
US 2004/0265824 A1    Dec. 30, 2004

Related U.S. Application Data

(60) Provisional application No. 60/317,494, filed on Sep. 7, 2001, provisional application No. 60/383,805, filed on May 30, 2002.

(51) Int. Cl.
*A61K 49/00* (2006.01)
*C12Q 1/37* (2006.01)
(52) U.S. Cl. .......................................... 424/9.1; 435/23
(58) Field of Classification Search ........................ None
See application file for complete search history.

(56) References Cited

U.S. PATENT DOCUMENTS
6,333,152 B1    12/2001    Vogelstein et al.

FOREIGN PATENT DOCUMENTS
WO    WO 98/53319    11/1998

OTHER PUBLICATIONS

Fukumura et al, Behaviour of urinary dipeptidase in patients with chronic renal failure. Ann Clin Biochem. Mar. 1999;36 ( Pt 2):221-5.*
USPTO in house search of Medline, EMBASE, Biosis, and Caplus via STN. Performed Apr. 30, 2008.*
Chen et al, Discordant protein and mRNA expression in lung adenocarcinomas. Mol Cell Proteomics. Apr. 2002;1(4):304-13.*
Buckhaults et al. Secreted and Cell Surface Genes Expressed in Benign and Malignant Colorectal Tumors. Cancer Research. Oct. 1, 2001, vol. 61, pages.
Ishigami et al. Predictive value of vascular endothelial growth factor (VEGF) in metastasis and prognosis of human colorectal cancer. British Journal of Cancer, 1998, vol. 78, No. 10, pp. 1379-1384.
Otte et al. Expression of keratinocyte growth factor and its receptor in colorectal cancer. European Journal of Clinical Investigation. 2000, vol. 30, pp. 222-229.
Mciver, CM, et al., "Dipeptidase 1: a candidate tumor-specific molecular marker in colorectal carcinoma," *Cancer Letters*, 209 (2004) 67-74.

* cited by examiner

*Primary Examiner* — Sheridan Swope
(74) *Attorney, Agent, or Firm* — Banner & Witcoff, Ltd.

(57) ABSTRACT

Particular genes are aberrantly and consistently expressed in both adenomas and carcinomas of the colon. Products of such genes provide stool and serum markers for colorectal neoplasia. One particular tumor marker, Renal Dipeptidase (RDP), is expressed at high levels in tumors and at greatly reduced levels in normal tissues. The elevated expression of RDP occurs early and remains elevated during the neoplastic process. RDP may therefore be especially useful as a diagnostic tool for the early detection of colorectal neoplasia, even of presymptomatic colorectal neoplasia.

18 Claims, 9 Drawing Sheets

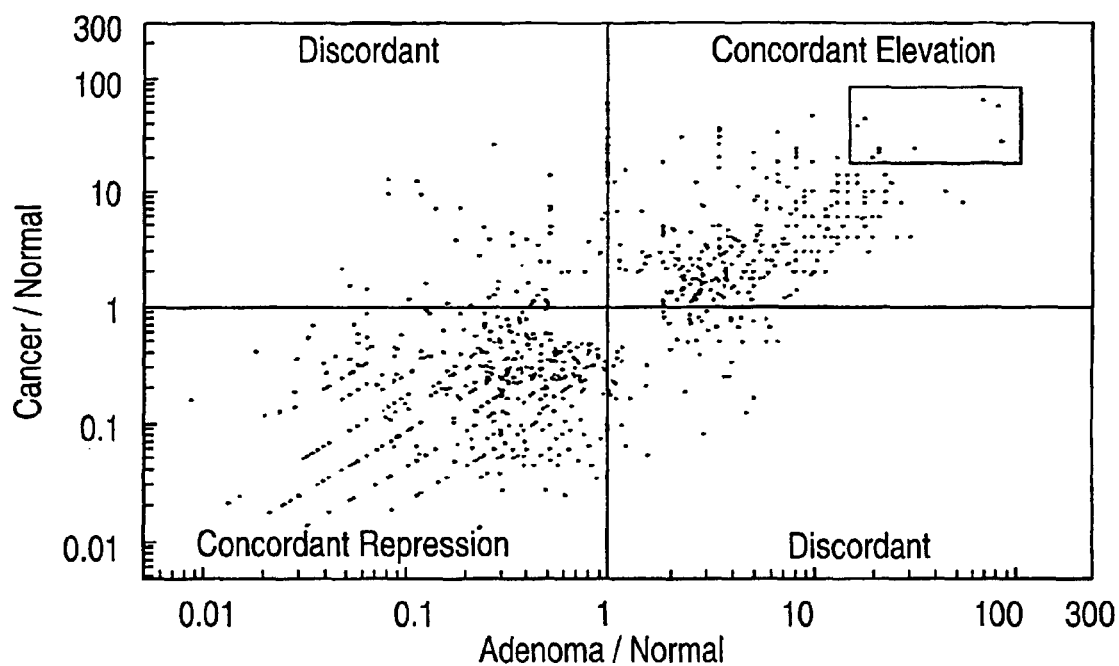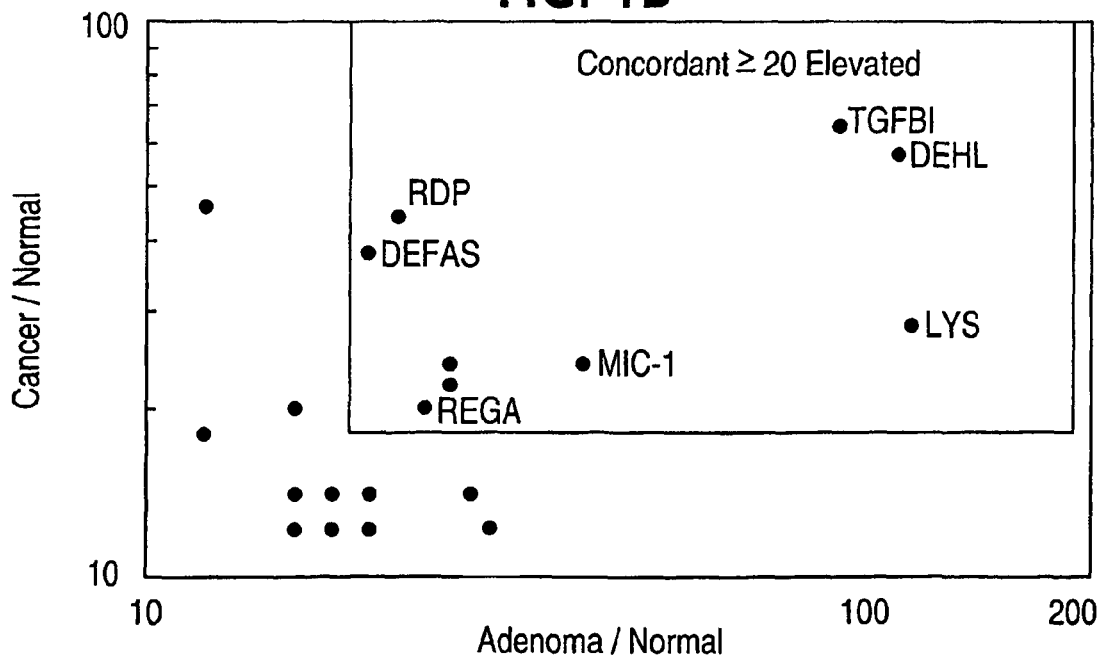

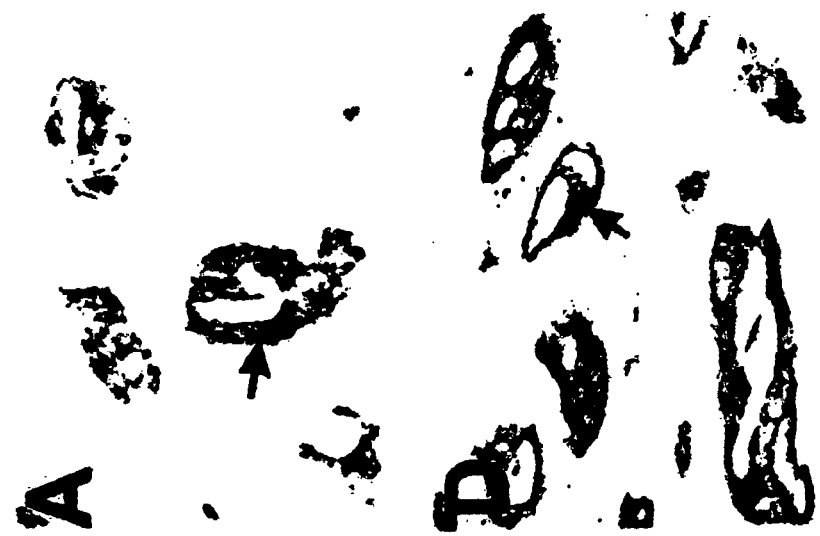
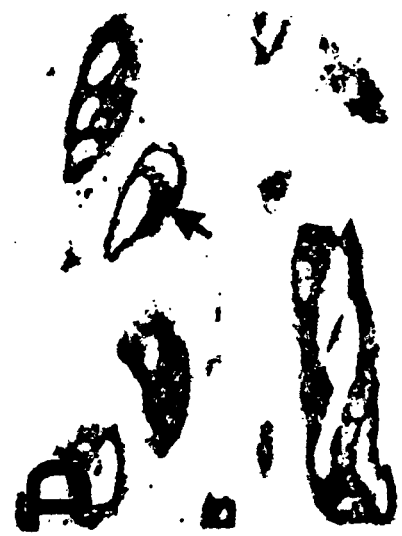

Compare Inhibs

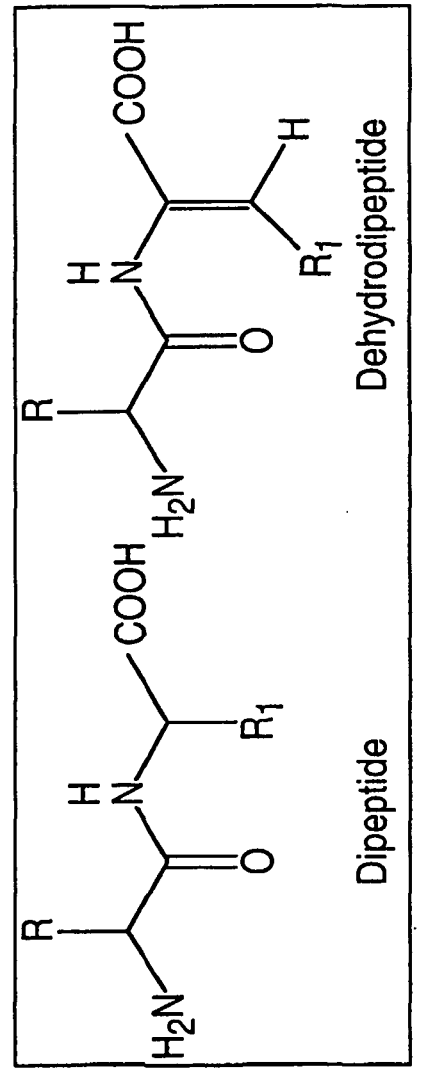
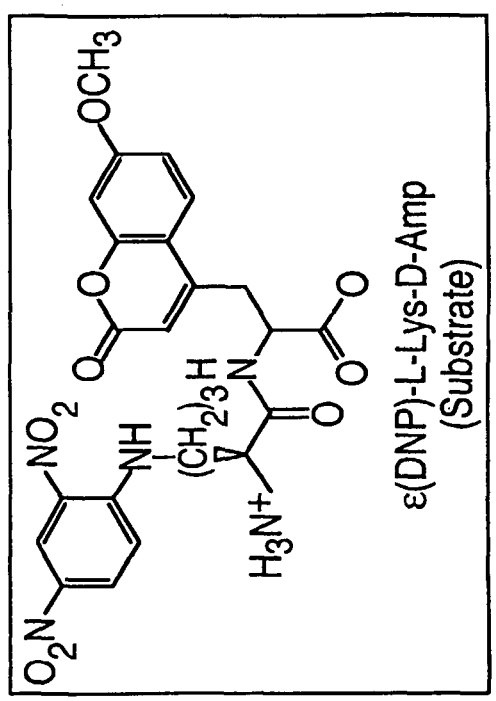
FIG. 8
Renal Dipeptidase Substrates

FIG. 9
Renal Dipeptidase Enzyme Activity in Human Tumors
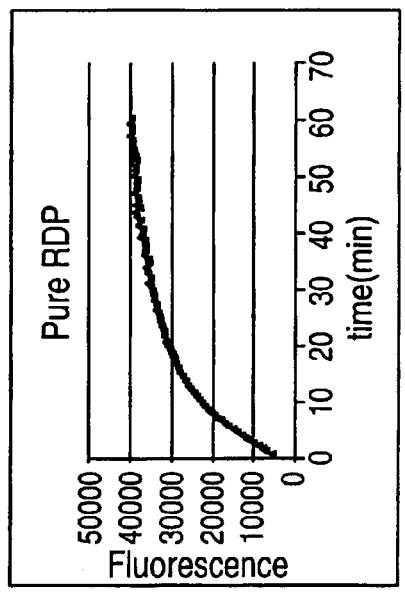
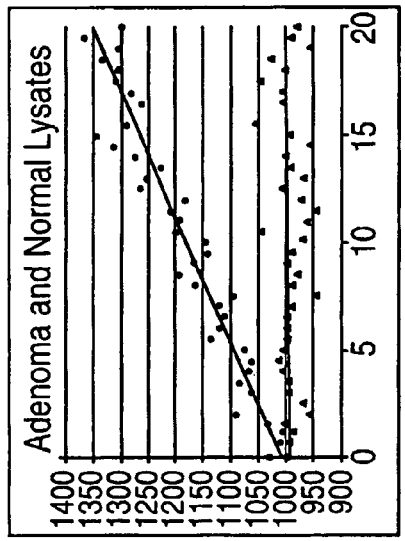
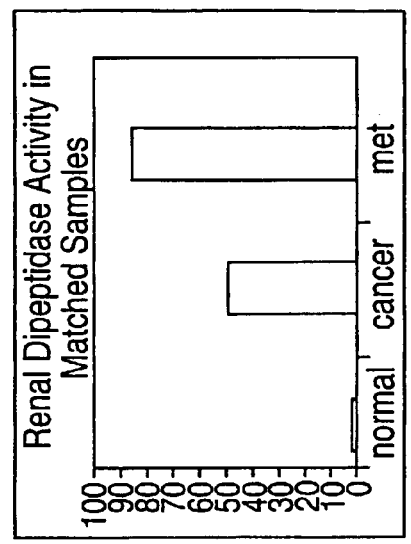

SEQUENCE LISTING

```
<160> NUMBER OF SEQ ID NOS: 334

<210> SEQ ID NO 1
<211> LENGTH: 10
<212> TYPE: DNA
<213> ORGANISM: Homo sapiens

<400> SEQUENCE: 1
atgtaaaaaa                                                          10

<210> SEQ ID NO 2
<211> LENGTH: 10
<212> TYPE: DNA
<213> ORGANISM: Homo sapiens

<400> SEQUENCE: 2
taatttttgc                                                          10

<210> SEQ ID NO 3
<211> LENGTH: 10
<212> TYPE: DNA
<213> ORGANISM: Homo sapiens

<400> SEQUENCE: 3
gtgtgtttgt                                                          10

<210> SEQ ID NO 4
<211> LENGTH: 10
<212> TYPE: DNA
<213> ORGANISM: Homo sapiens

<400> SEQUENCE: 4
gtgctcattc                                                          10

<210> SEQ ID NO 5
<211> LENGTH: 10
<212> TYPE: DNA
```

<213> ORGANISM: Homo sapiens

<400> SEQUENCE: 5
ttccagctgc                                                              10

<210> SEQ ID NO 6
<211> LENGTH: 10
<212> TYPE: DNA
<213> ORGANISM: Homo sapiens

<400> SEQUENCE: 6
accattggat                                                              10

<210> SEQ ID NO 7
<211> LENGTH: 10
<212> TYPE: DNA
<213> ORGANISM: Homo sapiens

<400> SEQUENCE: 7
tttccactaa                                                              10

<210> SEQ ID NO 8
<211> LENGTH: 10
<212> TYPE: DNA
<213> ORGANISM: Homo sapiens

<400> SEQUENCE: 8
caaggaccag                                                              10

<210> SEQ ID NO 9
<211> LENGTH: 10
<212> TYPE: DNA
<213> ORGANISM: Homo sapiens

<400> SEQUENCE: 9
aggaccatcg                                                              10

<210> SEQ ID NO 10
<211> LENGTH: 10
<212> TYPE: DNA
<213> ORGANISM: Homo sapiens

<400> SEQUENCE: 10
gtcatcacca                                                              10

<210> SEQ ID NO 11
<211> LENGTH: 10
<212> TYPE: DNA
<213> ORGANISM: Homo sapiens

<400> SEQUENCE: 11
ccttcaaatc                                                              10

<210> SEQ ID NO 12
<211> LENGTH: 10
<212> TYPE: DNA
<213> ORGANISM: Homo sapiens

<400> SEQUENCE: 12
tctgaattat                                                              10

<210> SEQ ID NO 13
<211> LENGTH: 10
<212> TYPE: DNA

```
<213> ORGANISM: Homo sapiens

<400> SEQUENCE: 13
ttatggtgtg                                                              10

<210> SEQ ID NO 14
<211> LENGTH: 10
<212> TYPE: DNA
<213> ORGANISM: Homo sapiens

<400> SEQUENCE: 14
ctggcaaagg                                                              10

<210> SEQ ID NO 15
<211> LENGTH: 10
<212> TYPE: DNA
<213> ORGANISM: Homo sapiens

<400> SEQUENCE: 15
aggtgactgg                                                              10

<210> SEQ ID NO 16
<211> LENGTH: 10
<212> TYPE: DNA
<213> ORGANISM: Homo sapiens

<400> SEQUENCE: 16
cttatggtcc                                                              10

<210> SEQ ID NO 17
<211> LENGTH: 10
<212> TYPE: DNA
<213> ORGANISM: Homo sapiens

<400> SEQUENCE: 17
atgatggcac                                                              10

<210> SEQ ID NO 18
<211> LENGTH: 10
<212> TYPE: DNA
<213> ORGANISM: Homo sapiens

<400> SEQUENCE: 18
gtccgagtgc                                                              10

<210> SEQ ID NO 19
<211> LENGTH: 10
<212> TYPE: DNA
<213> ORGANISM: Homo sapiens

<400> SEQUENCE: 19
atttcaagat                                                              10

<210> SEQ ID NO 20
<211> LENGTH: 10
<212> TYPE: DNA
<213> ORGANISM: Homo sapiens

<400> SEQUENCE: 20
caagagtttc                                                              10

<210> SEQ ID NO 21
<211> LENGTH: 10
<212> TYPE: DNA
```

```
<213> ORGANISM: Homo sapiens

<400> SEQUENCE: 21
gccatcctcc                                                          10

<210> SEQ ID NO 22
<211> LENGTH: 10
<212> TYPE: DNA
<213> ORGANISM: Homo sapiens

<400> SEQUENCE: 22
acccaactgc                                                          10

<210> SEQ ID NO 23
<211> LENGTH: 10
<212> TYPE: DNA
<213> ORGANISM: Homo sapiens

<400> SEQUENCE: 23
gcccacgtca                                                          10

<210> SEQ ID NO 24
<211> LENGTH: 10
<212> TYPE: DNA
<213> ORGANISM: Homo sapiens

<400> SEQUENCE: 24
tttggtttca                                                          10

<210> SEQ ID NO 25
<211> LENGTH: 10
<212> TYPE: DNA
<213> ORGANISM: Homo sapiens

<400> SEQUENCE: 25
ctcagaactt                                                          10

<210> SEQ ID NO 26
<211> LENGTH: 10
<212> TYPE: DNA
<213> ORGANISM: Homo sapiens

<400> SEQUENCE: 26
ccaacaccag                                                          10

<210> SEQ ID NO 27
<211> LENGTH: 10
<212> TYPE: DNA
<213> ORGANISM: Homo sapiens

<400> SEQUENCE: 27
gccacatact                                                          10

<210> SEQ ID NO 28
<211> LENGTH: 10
<212> TYPE: DNA
<213> ORGANISM: Homo sapiens

<400> SEQUENCE: 28
gtattggggc                                                          10

<210> SEQ ID NO 29
<211> LENGTH: 10
<212> TYPE: DNA
```

<210> SEQ ID NO 29
<211> LENGTH: 10
<212> TYPE: DNA
<213> ORGANISM: Homo sapiens

<400> SEQUENCE: 29
ccggcttgag                                                          10

<210> SEQ ID NO 30
<211> LENGTH: 10
<212> TYPE: DNA
<213> ORGANISM: Homo sapiens

<400> SEQUENCE: 30
gatatgtaaa                                                          10

<210> SEQ ID NO 31
<211> LENGTH: 10
<212> TYPE: DNA
<213> ORGANISM: Homo sapiens

<400> SEQUENCE: 31
cataggttta                                                          10

<210> SEQ ID NO 32
<211> LENGTH: 10
<212> TYPE: DNA
<213> ORGANISM: Homo sapiens

<400> SEQUENCE: 32
gtcctgaaca                                                          10

<210> SEQ ID NO 33
<211> LENGTH: 10
<212> TYPE: DNA
<213> ORGANISM: Homo sapiens

<400> SEQUENCE: 33
aaaagaaact                                                          10

<210> SEQ ID NO 34
<211> LENGTH: 10
<212> TYPE: DNA
<213> ORGANISM: Homo sapiens

<400> SEQUENCE: 34
aacgaggaat                                                          10

<210> SEQ ID NO 35
<211> LENGTH: 10
<212> TYPE: DNA
<213> ORGANISM: Homo sapiens

<400> SEQUENCE: 35
aagaagatag                                                          10

<210> SEQ ID NO 36
<211> LENGTH: 10
<212> TYPE: DNA
<213> ORGANISM: Homo sapiens

<400> SEQUENCE: 36
aataggtcca                                                          10

<210> SEQ ID NO 37
<211> LENGTH: 10
<212> TYPE: DNA

```
<213> ORGANISM: Homo sapiens

<400> SEQUENCE: 37
acaactcaat                                                              10

<210> SEQ ID NO 38
<211> LENGTH: 10
<212> TYPE: DNA
<213> ORGANISM: Homo sapiens

<400> SEQUENCE: 38
acaactcaat                                                              10

<210> SEQ ID NO 39
<211> LENGTH: 10
<212> TYPE: DNA
<213> ORGANISM: Homo sapiens

<400> SEQUENCE: 39
acatcatcga                                                              10

<210> SEQ ID NO 40
<211> LENGTH: 10
<212> TYPE: DNA
<213> ORGANISM: Homo sapiens

<400> SEQUENCE: 40
accattggat                                                              10

<210> SEQ ID NO 41
<211> LENGTH: 10
<212> TYPE: DNA
<213> ORGANISM: Homo sapiens

<400> SEQUENCE: 41
acctgtatcc                                                              10

<210> SEQ ID NO 42
<211> LENGTH: 10
<212> TYPE: DNA
<213> ORGANISM: Homo sapiens

<400> SEQUENCE: 42
actccaaaaa                                                              10

<210> SEQ ID NO 43
<211> LENGTH: 10
<212> TYPE: DNA
<213> ORGANISM: Homo sapiens

<400> SEQUENCE: 43
agcacctcca                                                              10

<210> SEQ ID NO 44
<211> LENGTH: 10
<212> TYPE: DNA
<213> ORGANISM: Homo sapiens

<400> SEQUENCE: 44
aggaccatcg                                                              10

<210> SEQ ID NO 45
<211> LENGTH: 10
<212> TYPE: DNA
```

```
<213> ORGANISM: Homo sapiens

<400> SEQUENCE: 45
agggcttcca                                                              10

<210> SEQ ID NO 46
<211> LENGTH: 10
<212> TYPE: DNA
<213> ORGANISM: Homo sapiens

<400> SEQUENCE: 46
atggctggta                                                              10

<210> SEQ ID NO 47
<211> LENGTH: 10
<212> TYPE: DNA
<213> ORGANISM: Homo sapiens

<400> SEQUENCE: 47
atgtaaaaaa                                                              10

<210> SEQ ID NO 48
<211> LENGTH: 10
<212> TYPE: DNA
<213> ORGANISM: Homo sapiens

<400> SEQUENCE: 48
atgtaaaaaa                                                              10

<210> SEQ ID NO 49
<211> LENGTH: 10
<212> TYPE: DNA
<213> ORGANISM: Homo sapiens

<400> SEQUENCE: 49
atgtaaaaaa                                                              10

<210> SEQ ID NO 50
<211> LENGTH: 10
<212> TYPE: DNA
<213> ORGANISM: Homo sapiens

<400> SEQUENCE: 50
attctccagt                                                              10

<210> SEQ ID NO 51
<211> LENGTH: 10
<212> TYPE: DNA
<213> ORGANISM: Homo sapiens

<400> SEQUENCE: 51
caaggaccag                                                              10

<210> SEQ ID NO 52
<211> LENGTH: 11
<212> TYPE: DNA
<213> ORGANISM: Homo sapiens

<400> SEQUENCE: 52
caatattttg t                                                            11

<210> SEQ ID NO 53
<211> LENGTH: 10
<212> TYPE: DNA
```

```
<213> ORGANISM: Homo sapiens

<400> SEQUENCE: 53
cagctcactg                                                          10

<210> SEQ ID NO 54
<211> LENGTH: 10
<212> TYPE: DNA
<213> ORGANISM: Homo sapiens

<400> SEQUENCE: 54
catttgtaat                                                          10

<210> SEQ ID NO 55
<211> LENGTH: 10
<212> TYPE: DNA
<213> ORGANISM: Homo sapiens

<400> SEQUENCE: 55
cctagctgga                                                          10

<210> SEQ ID NO 56
<211> LENGTH: 10
<212> TYPE: DNA
<213> ORGANISM: Homo sapiens

<400> SEQUENCE: 56
ccttcgagat                                                          10

<210> SEQ ID NO 57
<211> LENGTH: 10
<212> TYPE: DNA
<213> ORGANISM: Homo sapiens

<400> SEQUENCE: 57
ctcctcacct                                                          10

<210> SEQ ID NO 58
<211> LENGTH: 10
<212> TYPE: DNA
<213> ORGANISM: Homo sapiens

<400> SEQUENCE: 58
ctgacttgtg                                                          10

<210> SEQ ID NO 59
<211> LENGTH: 10
<212> TYPE: DNA
<213> ORGANISM: Homo sapiens

<400> SEQUENCE: 59
ctgggttaat                                                          10

<210> SEQ ID NO 60
<211> LENGTH: 11
<212> TYPE: DNA
<213> ORGANISM: Homo sapiens

<400> SEQUENCE: 60
ctgttgtatt g                                                        11

<210> SEQ ID NO 61
<211> LENGTH: 10
<212> TYPE: DNA
```

```
<213> ORGANISM: Homo sapiens

<400> SEQUENCE: 61
ctgttggtga                                                            10

<210> SEQ ID NO 62
<211> LENGTH: 10
<212> TYPE: DNA
<213> ORGANISM: Homo sapiens

<400> SEQUENCE: 62
gaaaaatggt                                                            10

<210> SEQ ID NO 63
<211> LENGTH: 10
<212> TYPE: DNA
<213> ORGANISM: Homo sapiens

<400> SEQUENCE: 63
gagtcaggag                                                            10

<210> SEQ ID NO 64
<211> LENGTH: 10
<212> TYPE: DNA
<213> ORGANISM: Homo sapiens

<400> SEQUENCE: 64
gcataatagg                                                            10

<210> SEQ ID NO 65
<211> LENGTH: 9
<212> TYPE: DNA
<213> ORGANISM: Homo sapiens

<400> SEQUENCE: 65 gcatttaat                                                              9

<210> SEQ ID NO 66
<211> LENGTH: 9
<212> TYPE: DNA
<213> ORGANISM: Homo sapiens

<400> SEQUENCE: 66 gcatttaat                                                              9

<210> SEQ ID NO 67
<211> LENGTH: 10
<212> TYPE: DNA
<213> ORGANISM: Homo sapiens

<400> SEQUENCE: 67
gcatttgaca                                                            10

<210> SEQ ID NO 68
<211> LENGTH: 10
<212> TYPE: DNA
<213> ORGANISM: Homo sapiens

<400> SEQUENCE: 68
gcttttaagg                                                            10

<210> SEQ ID NO 69
<211> LENGTH: 10
<212> TYPE: DNA
```

-continued

<213> ORGANISM: Homo sapiens

<400> SEQUENCE: 69
ggaccactga                                                              10

<210> SEQ ID NO 70
<211> LENGTH: 10
<212> TYPE: DNA
<213> ORGANISM: Homo sapiens

<400> SEQUENCE: 70
gggggtaact                                                              10

<210> SEQ ID NO 71
<211> LENGTH: 10
<212> TYPE: DNA
<213> ORGANISM: Homo sapiens

<400> SEQUENCE: 71
gtgcgctgag                                                              10

<210> SEQ ID NO 72
<211> LENGTH: 10
<212> TYPE: DNA
<213> ORGANISM: Homo sapiens

<400> SEQUENCE: 72
gtgctcattc                                                              10

<210> SEQ ID NO 73
<211> LENGTH: 10
<212> TYPE: DNA
<213> ORGANISM: Homo sapiens

<400> SEQUENCE: 73
gtgctcattc                                                              10

<210> SEQ ID NO 74
<211> LENGTH: 10
<212> TYPE: DNA
<213> ORGANISM: Homo sapiens

<400> SEQUENCE: 74
gtgtgtttgt                                                              10

<210> SEQ ID NO 75
<211> LENGTH: 10
<212> TYPE: DNA
<213> ORGANISM: Homo sapiens

<400> SEQUENCE: 75
gttcgtgcca                                                              10

<210> SEQ ID NO 76
<211> LENGTH: 10
<212> TYPE: DNA
<213> ORGANISM: Homo sapiens

<400> SEQUENCE: 76
gttcgtgcca                                                              10

<210> SEQ ID NO 77
<211> LENGTH: 10
<212> TYPE: DNA

```
<213> ORGANISM: Homo sapiens

<400> SEQUENCE: 77
taataaaggt                                                           10

<210> SEQ ID NO 78
<211> LENGTH: 10
<212> TYPE: DNA
<213> ORGANISM: Homo sapiens

<400> SEQUENCE: 78
taatttttgc                                                           10

<210> SEQ ID NO 79
<211> LENGTH: 10
<212> TYPE: DNA
<213> ORGANISM: Homo sapiens

<400> SEQUENCE: 79
tcacaagcaa                                                           10

<210> SEQ ID NO 80
<211> LENGTH: 10
<212> TYPE: DNA
<213> ORGANISM: Homo sapiens

<400> SEQUENCE: 80
tcagatcttt                                                           10

<210> SEQ ID NO 81
<211> LENGTH: 10
<212> TYPE: DNA
<213> ORGANISM: Homo sapiens

<400> SEQUENCE: 81
tcctgcccca                                                           10

<210> SEQ ID NO 82
<211> LENGTH: 10
<212> TYPE: DNA
<213> ORGANISM: Homo sapiens

<400> SEQUENCE: 82
tgaaataaaa                                                           10

<210> SEQ ID NO 83
<211> LENGTH: 10
<212> TYPE: DNA
<213> ORGANISM: Homo sapiens

<400> SEQUENCE: 83
tgaaataaaa                                                           10

<210> SEQ ID NO 84
<211> LENGTH: 10
<212> TYPE: DNA
<213> ORGANISM: Homo sapiens

<400> SEQUENCE: 84
tgatgtctgg                                                           10

<210> SEQ ID NO 85
<211> LENGTH: 10
<212> TYPE: DNA
```

```
<213> ORGANISM: Homo sapiens

<400> SEQUENCE: 85
tgtaatcaat                                                        10

<210> SEQ ID NO 86
<211> LENGTH: 10
<212> TYPE: DNA
<213> ORGANISM: Homo sapiens

<400> SEQUENCE: 86
ttaccatatc                                                        10

<210> SEQ ID NO 87
<211> LENGTH: 10
<212> TYPE: DNA
<213> ORGANISM: Homo sapiens

<400> SEQUENCE: 87
ttatgggatc                                                        10

<210> SEQ ID NO 88
<211> LENGTH: 10
<212> TYPE: DNA
<213> ORGANISM: Homo sapiens

<400> SEQUENCE: 88
ttcaattaaa                                                        10

<210> SEQ ID NO 89
<211> LENGTH: 9
<212> TYPE: DNA
<213> ORGANISM: Homo sapiens

<400> SEQUENCE: 89 ttccagctc                                                          9

<210> SEQ ID NO 90
<211> LENGTH: 9
<212> TYPE: DNA
<213> ORGANISM: Homo sapiens

<400> SEQUENCE: 90 ttccagctc                                                          9

<210> SEQ ID NO 91
<211> LENGTH: 9
<212> TYPE: DNA
<213> ORGANISM: Homo sapiens

<400> SEQUENCE: 91 ttccagctc                                                          9

<210> SEQ ID NO 92
<211> LENGTH: 10
<212> TYPE: DNA
<213> ORGANISM: Homo sapiens

<400> SEQUENCE: 92
tttccactaa                                                        10

<210> SEQ ID NO 93
<211> LENGTH: 10
<212> TYPE: DNA
```

```
<213> ORGANISM: Homo sapiens

<400> SEQUENCE: 93
tttccactaa                                                          10

<210> SEQ ID NO 94
<211> LENGTH: 10
<212> TYPE: DNA
<213> ORGANISM: Homo sapiens

<400> SEQUENCE: 94
tttttaatgt                                                          10

<210> SEQ ID NO 95
<211> LENGTH: 10
<212> TYPE: DNA
<213> ORGANISM: Homo sapiens

<400> SEQUENCE: 95
aaatctggca                                                          10

<210> SEQ ID NO 96
<211> LENGTH: 10
<212> TYPE: DNA
<213> ORGANISM: Homo sapiens

<400> SEQUENCE: 96
aacgtgcagg                                                          10

<210> SEQ ID NO 97
<211> LENGTH: 10
<212> TYPE: DNA
<213> ORGANISM: Homo sapiens

<400> SEQUENCE: 97
aagaaagctc                                                          10

<210> SEQ ID NO 98
<211> LENGTH: 10
<212> TYPE: DNA
<213> ORGANISM: Homo sapiens

<400> SEQUENCE: 98
aagaaagctc                                                          10

<210> SEQ ID NO 99
<211> LENGTH: 10
<212> TYPE: DNA
<213> ORGANISM: Homo sapiens

<400> SEQUENCE: 99
aagaagcagg                                                          10

<210> SEQ ID NO 100
<211> LENGTH: 10
<212> TYPE: DNA
<213> ORGANISM: Homo sapiens

<400> SEQUENCE: 100
aaggtagcag                                                          10

<210> SEQ ID NO 101
<211> LENGTH: 10
<212> TYPE: DNA
```

<213> ORGANISM: Homo sapiens

<400> SEQUENCE: 101
aataaaggct    10

<210> SEQ ID NO 102
<211> LENGTH: 10
<212> TYPE: DNA
<213> ORGANISM: Homo sapiens

<400> SEQUENCE: 102
aatagtttcc    10

<210> SEQ ID NO 103
<211> LENGTH: 10
<212> TYPE: DNA
<213> ORGANISM: Homo sapiens

<400> SEQUENCE: 103
aatcacaaat    10

<210> SEQ ID NO 104
<211> LENGTH: 10
<212> TYPE: DNA
<213> ORGANISM: Homo sapiens

<400> SEQUENCE: 104
aatgagaagg    10

<210> SEQ ID NO 105
<211> LENGTH: 10
<212> TYPE: DNA
<213> ORGANISM: Homo sapiens

<400> SEQUENCE: 105
acaattggtc    10

<210> SEQ ID NO 106
<211> LENGTH: 10
<212> TYPE: DNA
<213> ORGANISM: Homo sapiens

<400> SEQUENCE: 106
acacccatca    10

<210> SEQ ID NO 107
<211> LENGTH: 10
<212> TYPE: DNA
<213> ORGANISM: Homo sapiens

<400> SEQUENCE: 107
acagggtgac    10

<210> SEQ ID NO 108
<211> LENGTH: 10
<212> TYPE: DNA
<213> ORGANISM: Homo sapiens

<400> SEQUENCE: 108
acattgggtg    10

<210> SEQ ID NO 109
<211> LENGTH: 10
<212> TYPE: DNA

<213> ORGANISM: Homo sapiens

<400> SEQUENCE: 109 acattgggtg					10

<210> SEQ ID NO 110
<211> LENGTH: 10
<212> TYPE: DNA
<213> ORGANISM: Homo sapiens

<400> SEQUENCE: 110 acccaactgc					10

<210> SEQ ID NO 111
<211> LENGTH: 10
<212> TYPE: DNA
<213> ORGANISM: Homo sapiens

<400> SEQUENCE: 111 acccacgtca					10

<210> SEQ ID NO 112
<211> LENGTH: 10
<212> TYPE: DNA
<213> ORGANISM: Homo sapiens

<400> SEQUENCE: 112 acccccccgc					10

<210> SEQ ID NO 113
<211> LENGTH: 10
<212> TYPE: DNA
<213> ORGANISM: Homo sapiens

<400> SEQUENCE: 113 acccccccgc					10

<210> SEQ ID NO 114
<211> LENGTH: 10
<212> TYPE: DNA
<213> ORGANISM: Homo sapiens

<400> SEQUENCE: 114 acctgcatcc					10

<210> SEQ ID NO 115
<211> LENGTH: 10
<212> TYPE: DNA
<213> ORGANISM: Homo sapiens

<400> SEQUENCE: 115 acctggggag					10

<210> SEQ ID NO 116
<211> LENGTH: 10
<212> TYPE: DNA
<213> ORGANISM: Homo sapiens

<400> SEQUENCE: 116 acctggggag					10

<210> SEQ ID NO 117
<211> LENGTH: 10
<212> TYPE: DNA

```
<213> ORGANISM: Homo sapiens

<400> SEQUENCE: 117
acggtccagg                                                          10

<210> SEQ ID NO 118
<211> LENGTH: 10
<212> TYPE: DNA
<213> ORGANISM: Homo sapiens

<400> SEQUENCE: 118
actcttgttg                                                          10

<210> SEQ ID NO 119
<211> LENGTH: 10
<212> TYPE: DNA
<213> ORGANISM: Homo sapiens

<400> SEQUENCE: 119
actgtggcgg                                                          10

<210> SEQ ID NO 120
<211> LENGTH: 10
<212> TYPE: DNA
<213> ORGANISM: Homo sapiens

<400> SEQUENCE: 120
agaatagctt                                                          10

<210> SEQ ID NO 121
<211> LENGTH: 10
<212> TYPE: DNA
<213> ORGANISM: Homo sapiens

<400> SEQUENCE: 121
agcaggagca                                                          10

<210> SEQ ID NO 122
<211> LENGTH: 10
<212> TYPE: DNA
<213> ORGANISM: Homo sapiens

<400> SEQUENCE: 122
agcaggagca                                                          10

<210> SEQ ID NO 123
<211> LENGTH: 10
<212> TYPE: DNA
<213> ORGANISM: Homo sapiens

<400> SEQUENCE: 123
agcccgacca                                                          10

<210> SEQ ID NO 124
<211> LENGTH: 10
<212> TYPE: DNA
<213> ORGANISM: Homo sapiens

<400> SEQUENCE: 124
aggatggtcc                                                          10

<210> SEQ ID NO 125
<211> LENGTH: 10
<212> TYPE: DNA
```

-continued

<213> ORGANISM: Homo sapiens

<400> SEQUENCE: 125
aggccaaggg                                                              10

<210> SEQ ID NO 126
<211> LENGTH: 10
<212> TYPE: DNA
<213> ORGANISM: Homo sapiens

<400> SEQUENCE: 126
aggtgactgg                                                              10

<210> SEQ ID NO 127
<211> LENGTH: 10
<212> TYPE: DNA
<213> ORGANISM: Homo sapiens

<400> SEQUENCE: 127
agtgggctca                                                              10

<210> SEQ ID NO 128
<211> LENGTH: 10
<212> TYPE: DNA
<213> ORGANISM: Homo sapiens

<400> SEQUENCE: 128
atactccact                                                              10

<210> SEQ ID NO 129
<211> LENGTH: 10
<212> TYPE: DNA
<213> ORGANISM: Homo sapiens

<400> SEQUENCE: 129
atataatctg                                                              10

<210> SEQ ID NO 130
<211> LENGTH: 10
<212> TYPE: DNA
<213> ORGANISM: Homo sapiens

<400> SEQUENCE: 130
atcgtggcgg                                                              10

<210> SEQ ID NO 131
<211> LENGTH: 10
<212> TYPE: DNA
<213> ORGANISM: Homo sapiens

<400> SEQUENCE: 131
atgacgctca                                                              10

<210> SEQ ID NO 132
<211> LENGTH: 10
<212> TYPE: DNA
<213> ORGANISM: Homo sapiens

<400> SEQUENCE: 132
atgatggcac                                                              10

<210> SEQ ID NO 133
<211> LENGTH: 10
<212> TYPE: DNA

```
<213> ORGANISM: Homo sapiens

<400> SEQUENCE: 133
atgcggagtc                                                          10

<210> SEQ ID NO 134
<211> LENGTH: 10
<212> TYPE: DNA
<213> ORGANISM: Homo sapiens

<400> SEQUENCE: 134
atgcgggaga                                                          10

<210> SEQ ID NO 135
<211> LENGTH: 10
<212> TYPE: DNA
<213> ORGANISM: Homo sapiens

<400> SEQUENCE: 135
atggcacgga                                                          10

<210> SEQ ID NO 136
<211> LENGTH: 10
<212> TYPE: DNA
<213> ORGANISM: Homo sapiens

<400> SEQUENCE: 136
atggtctacg                                                          10

<210> SEQ ID NO 137
<211> LENGTH: 10
<212> TYPE: DNA
<213> ORGANISM: Homo sapiens

<400> SEQUENCE: 137
atggtggggg                                                          10

<210> SEQ ID NO 138
<211> LENGTH: 10
<212> TYPE: DNA
<213> ORGANISM: Homo sapiens

<400> SEQUENCE: 138
atgtgcgtgg                                                          10

<210> SEQ ID NO 139
<211> LENGTH: 10
<212> TYPE: DNA
<213> ORGANISM: Homo sapiens

<400> SEQUENCE: 139
atgtgggctc                                                          10

<210> SEQ ID NO 140
<211> LENGTH: 10
<212> TYPE: DNA
<213> ORGANISM: Homo sapiens

<400> SEQUENCE: 140
atgtgggctc                                                          10

<210> SEQ ID NO 141
<211> LENGTH: 10
<212> TYPE: DNA
```

<213> ORGANISM: Homo sapiens

<400> SEQUENCE: 141
attggagtgc                                                              10

<210> SEQ ID NO 142
<211> LENGTH: 10
<212> TYPE: DNA
<213> ORGANISM: Homo sapiens

<400> SEQUENCE: 142
atttcaagat                                                              10

<210> SEQ ID NO 143
<211> LENGTH: 10
<212> TYPE: DNA
<213> ORGANISM: Homo sapiens

<400> SEQUENCE: 143
atttcaagat                                                              10

<210> SEQ ID NO 144
<211> LENGTH: 10
<212> TYPE: DNA
<213> ORGANISM: Homo sapiens

<400> SEQUENCE: 144
caaataaaag                                                              10

<210> SEQ ID NO 145
<211> LENGTH: 10
<212> TYPE: DNA
<213> ORGANISM: Homo sapiens

<400> SEQUENCE: 145
caagagtttc                                                              10

<210> SEQ ID NO 146
<211> LENGTH: 10
<212> TYPE: DNA
<213> ORGANISM: Homo sapiens

<400> SEQUENCE: 146
cacccctgat                                                              10

<210> SEQ ID NO 147
<211> LENGTH: 10
<212> TYPE: DNA
<213> ORGANISM: Homo sapiens

<400> SEQUENCE: 147
cagtgcgttc                                                              10

<210> SEQ ID NO 148
<211> LENGTH: 10
<212> TYPE: DNA
<213> ORGANISM: Homo sapiens

<400> SEQUENCE: 148
cataggttta                                                              10

<210> SEQ ID NO 149
<211> LENGTH: 10
<212> TYPE: DNA

<213> ORGANISM: Homo sapiens

<400> SEQUENCE: 149
ccaaagctat                                                          10

<210> SEQ ID NO 150
<211> LENGTH: 10
<212> TYPE: DNA
<213> ORGANISM: Homo sapiens

<400> SEQUENCE: 150
ccaacaccag                                                          10

<210> SEQ ID NO 151
<211> LENGTH: 10
<212> TYPE: DNA
<213> ORGANISM: Homo sapiens

<400> SEQUENCE: 151
ccactgcacc                                                          10

<210> SEQ ID NO 152
<211> LENGTH: 10
<212> TYPE: DNA
<213> ORGANISM: Homo sapiens

<400> SEQUENCE: 152
ccaggggaga                                                          10

<210> SEQ ID NO 153
<211> LENGTH: 10
<212> TYPE: DNA
<213> ORGANISM: Homo sapiens

<400> SEQUENCE: 153
ccattccact                                                          10

<210> SEQ ID NO 154
<211> LENGTH: 10
<212> TYPE: DNA
<213> ORGANISM: Homo sapiens

<400> SEQUENCE: 154
cccaacgcgc                                                          10

<210> SEQ ID NO 155
<211> LENGTH: 10
<212> TYPE: DNA
<213> ORGANISM: Homo sapiens

<400> SEQUENCE: 155
cccccgaagc                                                          10

<210> SEQ ID NO 156
<211> LENGTH: 10
<212> TYPE: DNA
<213> ORGANISM: Homo sapiens

<400> SEQUENCE: 156
cccccgcgga                                                          10

<210> SEQ ID NO 157
<211> LENGTH: 10
<212> TYPE: DNA

<213> ORGANISM: Homo sapiens

<400> SEQUENCE: 157
cccctgcat                                                                10

<210> SEQ ID NO 158
<211> LENGTH: 10
<212> TYPE: DNA
<213> ORGANISM: Homo sapiens

<400> SEQUENCE: 158
cccgcctctt                                                                10

<210> SEQ ID NO 159
<211> LENGTH: 10
<212> TYPE: DNA
<213> ORGANISM: Homo sapiens

<400> SEQUENCE: 159
ccctcccgaa                                                                10

<210> SEQ ID NO 160
<211> LENGTH: 10
<212> TYPE: DNA
<213> ORGANISM: Homo sapiens

<400> SEQUENCE: 160
ccgctgcact                                                                10

<210> SEQ ID NO 161
<211> LENGTH: 10
<212> TYPE: DNA
<213> ORGANISM: Homo sapiens

<400> SEQUENCE: 161
ccggcttgag                                                                10

<210> SEQ ID NO 162
<211> LENGTH: 10
<212> TYPE: DNA
<213> ORGANISM: Homo sapiens

<400> SEQUENCE: 162
cctccagcta                                                                10

<210> SEQ ID NO 163
<211> LENGTH: 10
<212> TYPE: DNA
<213> ORGANISM: Homo sapiens

<400> SEQUENCE: 163
cctccagtac                                                                10

<210> SEQ ID NO 164
<211> LENGTH: 10
<212> TYPE: DNA
<213> ORGANISM: Homo sapiens

<400> SEQUENCE: 164
cctgccccc                                                                 10

<210> SEQ ID NO 165
<211> LENGTH: 10
<212> TYPE: DNA

```
<213> ORGANISM: Homo sapiens

<400> SEQUENCE: 165
cctgctgcag                                                          10

<210> SEQ ID NO 166
<211> LENGTH: 10
<212> TYPE: DNA
<213> ORGANISM: Homo sapiens

<400> SEQUENCE: 166
cctgcttgtc                                                          10

<210> SEQ ID NO 167
<211> LENGTH: 10
<212> TYPE: DNA
<213> ORGANISM: Homo sapiens

<400> SEQUENCE: 167
cctgcttgtc                                                          10

<210> SEQ ID NO 168
<211> LENGTH: 10
<212> TYPE: DNA
<213> ORGANISM: Homo sapiens

<400> SEQUENCE: 168
cctggaagag                                                          10

<210> SEQ ID NO 169
<211> LENGTH: 10
<212> TYPE: DNA
<213> ORGANISM: Homo sapiens

<400> SEQUENCE: 169
cctgtctgcc                                                          10

<210> SEQ ID NO 170
<211> LENGTH: 10
<212> TYPE: DNA
<213> ORGANISM: Homo sapiens

<400> SEQUENCE: 170
cctgtgacag                                                          10

<210> SEQ ID NO 171
<211> LENGTH: 10
<212> TYPE: DNA
<213> ORGANISM: Homo sapiens

<400> SEQUENCE: 171
ccttcaaatc                                                          10

<210> SEQ ID NO 172
<211> LENGTH: 10
<212> TYPE: DNA
<213> ORGANISM: Homo sapiens

<400> SEQUENCE: 172
cgaggggcca                                                          10

<210> SEQ ID NO 173
<211> LENGTH: 10
<212> TYPE: DNA
```

<213> ORGANISM: Homo sapiens

<400> SEQUENCE: 173
cgctgtgggg                                                          10

<210> SEQ ID NO 174
<211> LENGTH: 10
<212> TYPE: DNA
<213> ORGANISM: Homo sapiens

<400> SEQUENCE: 174
cggactcact                                                          10

<210> SEQ ID NO 175
<211> LENGTH: 10
<212> TYPE: DNA
<213> ORGANISM: Homo sapiens

<400> SEQUENCE: 175
cggactcact                                                          10

<210> SEQ ID NO 176
<211> LENGTH: 10
<212> TYPE: DNA
<213> ORGANISM: Homo sapiens

<400> SEQUENCE: 176
cgggagtcgg                                                          10

<210> SEQ ID NO 177
<211> LENGTH: 10
<212> TYPE: DNA
<213> ORGANISM: Homo sapiens

<400> SEQUENCE: 177
cggtgggacc                                                          10

<210> SEQ ID NO 178
<211> LENGTH: 10
<212> TYPE: DNA
<213> ORGANISM: Homo sapiens

<400> SEQUENCE: 178
cgtgggtggg                                                          10

<210> SEQ ID NO 179
<211> LENGTH: 10
<212> TYPE: DNA
<213> ORGANISM: Homo sapiens

<400> SEQUENCE: 179
ctaccctcac                                                          10

<210> SEQ ID NO 180
<211> LENGTH: 10
<212> TYPE: DNA
<213> ORGANISM: Homo sapiens

<400> SEQUENCE: 180
ctcagaactt                                                          10

<210> SEQ ID NO 181
<211> LENGTH: 10
<212> TYPE: DNA

<213> ORGANISM: Homo sapiens

<400> SEQUENCE: 181
ctgaacctcc                                                                    10

<210> SEQ ID NO 182
<211> LENGTH: 10
<212> TYPE: DNA
<213> ORGANISM: Homo sapiens

<400> SEQUENCE: 182
ctgacctgtg                                                                    10

<210> SEQ ID NO 183
<211> LENGTH: 10
<212> TYPE: DNA
<213> ORGANISM: Homo sapiens

<400> SEQUENCE: 183
ctggatctgg                                                                    10

<210> SEQ ID NO 184
<211> LENGTH: 10
<212> TYPE: DNA
<213> ORGANISM: Homo sapiens

<400> SEQUENCE: 184
ctggcaaagg                                                                    10

<210> SEQ ID NO 185
<211> LENGTH: 10
<212> TYPE: DNA
<213> ORGANISM: Homo sapiens

<400> SEQUENCE: 185
ctggccctcg                                                                    10

<210> SEQ ID NO 186
<211> LENGTH: 10
<212> TYPE: DNA
<213> ORGANISM: Homo sapiens

<400> SEQUENCE: 186
ctggccctcg                                                                    10

<210> SEQ ID NO 187
<211> LENGTH: 10
<212> TYPE: DNA
<213> ORGANISM: Homo sapiens

<400> SEQUENCE: 187
ctgcccctcg                                                                    10

<210> SEQ ID NO 188
<211> LENGTH: 10
<212> TYPE: DNA
<213> ORGANISM: Homo sapiens

<400> SEQUENCE: 188
ctggctatcc                                                                    10

<210> SEQ ID NO 189
<211> LENGTH: 10
<212> TYPE: DNA

<213> ORGANISM: Homo sapiens

<400> SEQUENCE: 189 ctgggcctct					10

<210> SEQ ID NO 190
<211> LENGTH: 10
<212> TYPE: DNA
<213> ORGANISM: Homo sapiens

<400> SEQUENCE: 190 ctgtacttgt					10

<210> SEQ ID NO 191
<211> LENGTH: 10
<212> TYPE: DNA
<213> ORGANISM: Homo sapiens

<400> SEQUENCE: 191 ctgtgtggct					10

<210> SEQ ID NO 192
<211> LENGTH: 10
<212> TYPE: DNA
<213> ORGANISM: Homo sapiens

<400> SEQUENCE: 192 ctgtgtggct					10

<210> SEQ ID NO 193
<211> LENGTH: 10
<212> TYPE: DNA
<213> ORGANISM: Homo sapiens

<400> SEQUENCE: 193 cttacaagca					10

<210> SEQ ID NO 194
<211> LENGTH: 10
<212> TYPE: DNA
<213> ORGANISM: Homo sapiens

<400> SEQUENCE: 194 cttagagggg					10

<210> SEQ ID NO 195
<211> LENGTH: 10
<212> TYPE: DNA
<213> ORGANISM: Homo sapiens

<400> SEQUENCE: 195 cttatggtcc					10

<210> SEQ ID NO 196
<211> LENGTH: 10
<212> TYPE: DNA
<213> ORGANISM: Homo sapiens

<400> SEQUENCE: 196 cttccagcta					10

<210> SEQ ID NO 197
<211> LENGTH: 10
<212> TYPE: DNA

<210> SEQ ID NO 197
<211> LENGTH: 10
<212> TYPE: DNA
<213> ORGANISM: Homo sapiens

<400> SEQUENCE: 197
cttcttgccc                                                            10

<210> SEQ ID NO 198
<211> LENGTH: 10
<212> TYPE: DNA
<213> ORGANISM: Homo sapiens

<400> SEQUENCE: 198
cttgacatac                                                            10

<210> SEQ ID NO 199
<211> LENGTH: 10
<212> TYPE: DNA
<213> ORGANISM: Homo sapiens

<400> SEQUENCE: 199
cttgattccc                                                            10

<210> SEQ ID NO 200
<211> LENGTH: 10
<212> TYPE: DNA
<213> ORGANISM: Homo sapiens

<400> SEQUENCE: 200
gacatcaagt                                                            10

<210> SEQ ID NO 201
<211> LENGTH: 10
<212> TYPE: DNA
<213> ORGANISM: Homo sapiens

<400> SEQUENCE: 201
gaccagccca                                                            10

<210> SEQ ID NO 202
<211> LENGTH: 10
<212> TYPE: DNA
<213> ORGANISM: Homo sapiens

<400> SEQUENCE: 202
gaccagtggc                                                            10

<210> SEQ ID NO 203
<211> LENGTH: 10
<212> TYPE: DNA
<213> ORGANISM: Homo sapiens

<400> SEQUENCE: 203
gacgcggcgc                                                            10

<210> SEQ ID NO 204
<211> LENGTH: 10
<212> TYPE: DNA
<213> ORGANISM: Homo sapiens

<400> SEQUENCE: 204
gagagctccc                                                            10

<210> SEQ ID NO 205
<211> LENGTH: 10
<212> TYPE: DNA

```
<213> ORGANISM: Homo sapiens

<400> SEQUENCE: 205
gagcaccgtg                                                          10

<210> SEQ ID NO 206
<211> LENGTH: 10
<212> TYPE: DNA
<213> ORGANISM: Homo sapiens

<400> SEQUENCE: 206
gatatgtaaa                                                          10

<210> SEQ ID NO 207
<211> LENGTH: 10
<212> TYPE: DNA
<213> ORGANISM: Homo sapiens

<400> SEQUENCE: 207
gatcccaact                                                          10

<210> SEQ ID NO 208
<211> LENGTH: 10
<212> TYPE: DNA
<213> ORGANISM: Homo sapiens

<400> SEQUENCE: 208
gatgaatccg                                                          10

<210> SEQ ID NO 209
<211> LENGTH: 10
<212> TYPE: DNA
<213> ORGANISM: Homo sapiens

<400> SEQUENCE: 209
gatgaccccc                                                          10

<210> SEQ ID NO 210
<211> LENGTH: 10
<212> TYPE: DNA
<213> ORGANISM: Homo sapiens

<400> SEQUENCE: 210
gcaagaaagt                                                          10

<210> SEQ ID NO 211
<211> LENGTH: 10
<212> TYPE: DNA
<213> ORGANISM: Homo sapiens

<400> SEQUENCE: 211
gcacaggtca                                                          10

<210> SEQ ID NO 212
<211> LENGTH: 10
<212> TYPE: DNA
<213> ORGANISM: Homo sapiens

<400> SEQUENCE: 212
gcacccttc                                                           10

<210> SEQ ID NO 213
<211> LENGTH: 10
<212> TYPE: DNA
```

```
<213> ORGANISM: Homo sapiens

<400> SEQUENCE: 213
gcacctgtcg                                                          10

<210> SEQ ID NO 214
<211> LENGTH: 10
<212> TYPE: DNA
<213> ORGANISM: Homo sapiens

<400> SEQUENCE: 214
gcacctgtcg                                                          10

<210> SEQ ID NO 215
<211> LENGTH: 10
<212> TYPE: DNA
<213> ORGANISM: Homo sapiens

<400> SEQUENCE: 215
gcagctcctg                                                          10

<210> SEQ ID NO 216
<211> LENGTH: 10
<212> TYPE: DNA
<213> ORGANISM: Homo sapiens

<400> SEQUENCE: 216
gcaggaggtg                                                          10

<210> SEQ ID NO 217
<211> LENGTH: 10
<212> TYPE: DNA
<213> ORGANISM: Homo sapiens

<400> SEQUENCE: 217
gcaggaggtg                                                          10

<210> SEQ ID NO 218
<211> LENGTH: 10
<212> TYPE: DNA
<213> ORGANISM: Homo sapiens

<400> SEQUENCE: 218
gcagggcctc                                                          10

<210> SEQ ID NO 219
<211> LENGTH: 10
<212> TYPE: DNA
<213> ORGANISM: Homo sapiens

<400> SEQUENCE: 219
gccacatact                                                          10

<210> SEQ ID NO 220
<211> LENGTH: 10
<212> TYPE: DNA
<213> ORGANISM: Homo sapiens

<400> SEQUENCE: 220
gccacgtgga                                                          10

<210> SEQ ID NO 221
<211> LENGTH: 10
<212> TYPE: DNA
```

<213> ORGANISM: Homo sapiens

<400> SEQUENCE: 221
gccagacacc          10

<210> SEQ ID NO 222
<211> LENGTH: 10
<212> TYPE: DNA
<213> ORGANISM: Homo sapiens

<400> SEQUENCE: 222
gccaggttgc          10

<210> SEQ ID NO 223
<211> LENGTH: 10
<212> TYPE: DNA
<213> ORGANISM: Homo sapiens

<400> SEQUENCE: 223
gccaggttgc          10

<210> SEQ ID NO 224
<211> LENGTH: 10
<212> TYPE: DNA
<213> ORGANISM: Homo sapiens

<400> SEQUENCE: 224
gccaggttgc          10

<210> SEQ ID NO 225
<211> LENGTH: 10
<212> TYPE: DNA
<213> ORGANISM: Homo sapiens

<400> SEQUENCE: 225
gccatcctcc          10

<210> SEQ ID NO 226
<211> LENGTH: 10
<212> TYPE: DNA
<213> ORGANISM: Homo sapiens

<400> SEQUENCE: 226
gcccacacag          10

<210> SEQ ID NO 227
<211> LENGTH: 10
<212> TYPE: DNA
<213> ORGANISM: Homo sapiens

<400> SEQUENCE: 227
gcccacgtca          10

<210> SEQ ID NO 228
<211> LENGTH: 10
<212> TYPE: DNA
<213> ORGANISM: Homo sapiens

<400> SEQUENCE: 228
gcccagggcc          10

<210> SEQ ID NO 229
<211> LENGTH: 10
<212> TYPE: DNA

<213> ORGANISM: Homo sapiens

<400> SEQUENCE: 229
gcccagggcc                                                               10

<210> SEQ ID NO 230
<211> LENGTH: 10
<212> TYPE: DNA
<213> ORGANISM: Homo sapiens

<400> SEQUENCE: 230
gcccagggcc                                                               10

<210> SEQ ID NO 231
<211> LENGTH: 10
<212> TYPE: DNA
<213> ORGANISM: Homo sapiens

<400> SEQUENCE: 231
gcccaggtca                                                               10

<210> SEQ ID NO 232
<211> LENGTH: 10
<212> TYPE: DNA
<213> ORGANISM: Homo sapiens

<400> SEQUENCE: 232
gcccagtggc                                                               10

<210> SEQ ID NO 233
<211> LENGTH: 10
<212> TYPE: DNA
<213> ORGANISM: Homo sapiens

<400> SEQUENCE: 233
gccgaccagg                                                               10

<210> SEQ ID NO 234
<211> LENGTH: 10
<212> TYPE: DNA
<213> ORGANISM: Homo sapiens

<400> SEQUENCE: 234
gccgggtggg                                                               10

<210> SEQ ID NO 235
<211> LENGTH: 10
<212> TYPE: DNA
<213> ORGANISM: Homo sapiens

<400> SEQUENCE: 235
gccgtggaga                                                               10

<210> SEQ ID NO 236
<211> LENGTH: 10
<212> TYPE: DNA
<213> ORGANISM: Homo sapiens

<400> SEQUENCE: 236
gcctggccat                                                               10

<210> SEQ ID NO 237
<211> LENGTH: 10
<212> TYPE: DNA

<213> ORGANISM: Homo sapiens

<400> SEQUENCE: 237 gcctggccat					10

<210> SEQ ID NO 238
<211> LENGTH: 10
<212> TYPE: DNA
<213> ORGANISM: Homo sapiens

<400> SEQUENCE: 238 gcgaaaccct					10

<210> SEQ ID NO 239
<211> LENGTH: 10
<212> TYPE: DNA
<213> ORGANISM: Homo sapiens

<400> SEQUENCE: 239 gcgaaactcg					10

<210> SEQ ID NO 240
<211> LENGTH: 10
<212> TYPE: DNA
<213> ORGANISM: Homo sapiens

<400> SEQUENCE: 240 gcgcagaggt					10

<210> SEQ ID NO 241
<211> LENGTH: 10
<212> TYPE: DNA
<213> ORGANISM: Homo sapiens

<400> SEQUENCE: 241 gctcttcccc					10

<210> SEQ ID NO 242
<211> LENGTH: 10
<212> TYPE: DNA
<213> ORGANISM: Homo sapiens

<400> SEQUENCE: 242 gctgcctttg					10

<210> SEQ ID NO 243
<211> LENGTH: 10
<212> TYPE: DNA
<213> ORGANISM: Homo sapiens

<400> SEQUENCE: 243 gctgcccttg					10

<210> SEQ ID NO 244
<211> LENGTH: 10
<212> TYPE: DNA
<213> ORGANISM: Homo sapiens

<400> SEQUENCE: 244 gctggcacat					10

<210> SEQ ID NO 245
<211> LENGTH: 10
<212> TYPE: DNA

```
<213> ORGANISM: Homo sapiens

<400> SEQUENCE: 245
gctggccccg                                                           10

<210> SEQ ID NO 246
<211> LENGTH: 10
<212> TYPE: DNA
<213> ORGANISM: Homo sapiens

<400> SEQUENCE: 246
gctgtgcctg                                                           10

<210> SEQ ID NO 247
<211> LENGTH: 10
<212> TYPE: DNA
<213> ORGANISM: Homo sapiens

<400> SEQUENCE: 247
gcttggggat                                                           10

<210> SEQ ID NO 248
<211> LENGTH: 10
<212> TYPE: DNA
<213> ORGANISM: Homo sapiens

<400> SEQUENCE: 248
ggaacagggg                                                           10

<210> SEQ ID NO 249
<211> LENGTH: 10
<212> TYPE: DNA
<213> ORGANISM: Homo sapiens

<400> SEQUENCE: 249
ggaacagggg                                                           10

<210> SEQ ID NO 250
<211> LENGTH: 10
<212> TYPE: DNA
<213> ORGANISM: Homo sapiens

<400> SEQUENCE: 250
ggaacagggg                                                           10

<210> SEQ ID NO 251
<211> LENGTH: 10
<212> TYPE: DNA
<213> ORGANISM: Homo sapiens

<400> SEQUENCE: 251
ggaactgtga                                                           10

<210> SEQ ID NO 252
<211> LENGTH: 10
<212> TYPE: DNA
<213> ORGANISM: Homo sapiens

<400> SEQUENCE: 252
ggaagagcac                                                           10

<210> SEQ ID NO 253
<211> LENGTH: 10
<212> TYPE: DNA
```

<213> ORGANISM: Homo sapiens

<400> SEQUENCE: 253
ggaggccgag          10

<210> SEQ ID NO 254
<211> LENGTH: 10
<212> TYPE: DNA
<213> ORGANISM: Homo sapiens

<400> SEQUENCE: 254
ggaggcgctc          10

<210> SEQ ID NO 255
<211> LENGTH: 10
<212> TYPE: DNA
<213> ORGANISM: Homo sapiens

<400> SEQUENCE: 255
ggatggctta          10

<210> SEQ ID NO 256
<211> LENGTH: 10
<212> TYPE: DNA
<213> ORGANISM: Homo sapiens

<400> SEQUENCE: 256
ggcaccgtgc          10

<210> SEQ ID NO 257
<211> LENGTH: 10
<212> TYPE: DNA
<213> ORGANISM: Homo sapiens

<400> SEQUENCE: 257
ggccctgcag          10

<210> SEQ ID NO 258
<211> LENGTH: 10
<212> TYPE: DNA
<213> ORGANISM: Homo sapiens

<400> SEQUENCE: 258
ggctcgggat          10

<210> SEQ ID NO 259
<211> LENGTH: 10
<212> TYPE: DNA
<213> ORGANISM: Homo sapiens

<400> SEQUENCE: 259
ggctgcctgc          10

<210> SEQ ID NO 260
<211> LENGTH: 10
<212> TYPE: DNA
<213> ORGANISM: Homo sapiens

<400> SEQUENCE: 260
ggctgcctgc          10

<210> SEQ ID NO 261
<211> LENGTH: 10
<212> TYPE: DNA

```
<213> ORGANISM: Homo sapiens

<400> SEQUENCE: 261
ggctgggcct                                                                  10

<210> SEQ ID NO 262
<211> LENGTH: 10
<212> TYPE: DNA
<213> ORGANISM: Homo sapiens

<400> SEQUENCE: 262
ggctgggcct                                                                  10

<210> SEQ ID NO 263
<211> LENGTH: 10
<212> TYPE: DNA
<213> ORGANISM: Homo sapiens

<400> SEQUENCE: 263
ggctgggcct                                                                  10

<210> SEQ ID NO 264
<211> LENGTH: 10
<212> TYPE: DNA
<213> ORGANISM: Homo sapiens

<400> SEQUENCE: 264
gggaagcaga                                                                  10

<210> SEQ ID NO 265
<211> LENGTH: 10
<212> TYPE: DNA
<213> ORGANISM: Homo sapiens

<400> SEQUENCE: 265
gggacgagtg                                                                  10

<210> SEQ ID NO 266
<211> LENGTH: 10
<212> TYPE: DNA
<213> ORGANISM: Homo sapiens

<400> SEQUENCE: 266
gggcgctgtg                                                                  10

<210> SEQ ID NO 267
<211> LENGTH: 10
<212> TYPE: DNA
<213> ORGANISM: Homo sapiens

<400> SEQUENCE: 267
ggggcagggc                                                                  10

<210> SEQ ID NO 268
<211> LENGTH: 10
<212> TYPE: DNA
<213> ORGANISM: Homo sapiens

<400> SEQUENCE: 268
ggtgaagagg                                                                  10

<210> SEQ ID NO 269
<211> LENGTH: 10
<212> TYPE: DNA
```

<213> ORGANISM: Homo sapiens

<400> SEQUENCE: 269 gtagcaggtg					10

<210> SEQ ID NO 270
<211> LENGTH: 10
<212> TYPE: DNA
<213> ORGANISM: Homo sapiens

<400> SEQUENCE: 270 gtattggggc					10

<210> SEQ ID NO 271
<211> LENGTH: 10
<212> TYPE: DNA
<213> ORGANISM: Homo sapiens

<400> SEQUENCE: 271 gtcatcacca					10

<210> SEQ ID NO 272
<211> LENGTH: 10
<212> TYPE: DNA
<213> ORGANISM: Homo sapiens

<400> SEQUENCE: 272 gtcatcacca					10

<210> SEQ ID NO 273
<211> LENGTH: 10
<212> TYPE: DNA
<213> ORGANISM: Homo sapiens

<400> SEQUENCE: 273 gtcatcacca					10

<210> SEQ ID NO 274
<211> LENGTH: 10
<212> TYPE: DNA
<213> ORGANISM: Homo sapiens

<400> SEQUENCE: 274 gtcatcacca					10

<210> SEQ ID NO 275
<211> LENGTH: 10
<212> TYPE: DNA
<213> ORGANISM: Homo sapiens

<400> SEQUENCE: 275 gtccgagtgc					10

<210> SEQ ID NO 276
<211> LENGTH: 10
<212> TYPE: DNA
<213> ORGANISM: Homo sapiens

<400> SEQUENCE: 276 gtcctgaaca					10

<210> SEQ ID NO 277
<211> LENGTH: 10
<212> TYPE: DNA

<213> ORGANISM: Homo sapiens

<400> SEQUENCE: 277
gtcctgaaca                                                          10

<210> SEQ ID NO 278
<211> LENGTH: 10
<212> TYPE: DNA
<213> ORGANISM: Homo sapiens

<400> SEQUENCE: 278
gtgcactgag                                                          10

<210> SEQ ID NO 279
<211> LENGTH: 10
<212> TYPE: DNA
<213> ORGANISM: Homo sapiens

<400> SEQUENCE: 279
gtgcactgag                                                          10

<210> SEQ ID NO 280
<211> LENGTH: 10
<212> TYPE: DNA
<213> ORGANISM: Homo sapiens

<400> SEQUENCE: 280
gtgcctgaga                                                          10

<210> SEQ ID NO 281
<211> LENGTH: 10
<212> TYPE: DNA
<213> ORGANISM: Homo sapiens

<400> SEQUENCE: 281
gtggcgggaa                                                          10

<210> SEQ ID NO 282
<211> LENGTH: 10
<212> TYPE: DNA
<213> ORGANISM: Homo sapiens

<400> SEQUENCE: 282
gtgggggcgc                                                          10

<210> SEQ ID NO 283
<211> LENGTH: 10
<212> TYPE: DNA
<213> ORGANISM: Homo sapiens

<400> SEQUENCE: 283
gtggtggcag                                                          10

<210> SEQ ID NO 284
<211> LENGTH: 10
<212> TYPE: DNA
<213> ORGANISM: Homo sapiens

<400> SEQUENCE: 284
gtggttcacg                                                          10

<210> SEQ ID NO 285
<211> LENGTH: 10
<212> TYPE: DNA

<213> ORGANISM: Homo sapiens

<400> SEQUENCE: 285
gtggttcacg    10

<210> SEQ ID NO 286
<211> LENGTH: 10
<212> TYPE: DNA
<213> ORGANISM: Homo sapiens

<400> SEQUENCE: 286 gtgttgggggg    10

<210> SEQ ID NO 287
<211> LENGTH: 10
<212> TYPE: DNA
<213> ORGANISM: Homo sapiens

<400> SEQUENCE: 287
gtttagaggg    10

<210> SEQ ID NO 288
<211> LENGTH: 10
<212> TYPE: DNA
<213> ORGANISM: Homo sapiens

<400> SEQUENCE: 288
taaattgcaa    10

<210> SEQ ID NO 289
<211> LENGTH: 10
<212> TYPE: DNA
<213> ORGANISM: Homo sapiens

<400> SEQUENCE: 289
taaggccttt    10

<210> SEQ ID NO 290
<211> LENGTH: 10
<212> TYPE: DNA
<213> ORGANISM: Homo sapiens

<400> SEQUENCE: 290
taaggccttt    10

<210> SEQ ID NO 291
<211> LENGTH: 10
<212> TYPE: DNA
<213> ORGANISM: Homo sapiens

<400> SEQUENCE: 291
taatcccagc    10

<210> SEQ ID NO 292
<211> LENGTH: 10
<212> TYPE: DNA
<213> ORGANISM: Homo sapiens

<400> SEQUENCE: 292
taatttgcat    10

<210> SEQ ID NO 293
<211> LENGTH: 10
<212> TYPE: DNA

<213> ORGANISM: Homo sapiens

<400> SEQUENCE: 293
tacggtgtgg                                                             10

<210> SEQ ID NO 294
<211> LENGTH: 10
<212> TYPE: DNA
<213> ORGANISM: Homo sapiens

<400> SEQUENCE: 294
tactcggcca                                                             10

<210> SEQ ID NO 295
<211> LENGTH: 10
<212> TYPE: DNA
<213> ORGANISM: Homo sapiens

<400> SEQUENCE: 295
tactgtggat                                                             10

<210> SEQ ID NO 296
<211> LENGTH: 10
<212> TYPE: DNA
<213> ORGANISM: Homo sapiens

<400> SEQUENCE: 296
tagactagca                                                             10

<210> SEQ ID NO 297
<211> LENGTH: 10
<212> TYPE: DNA
<213> ORGANISM: Homo sapiens

<400> SEQUENCE: 297
taggatgggg                                                             10

<210> SEQ ID NO 298
<211> LENGTH: 10
<212> TYPE: DNA
<213> ORGANISM: Homo sapiens

<400> SEQUENCE: 298
tatgatgagc                                                             10

<210> SEQ ID NO 299
<211> LENGTH: 10
<212> TYPE: DNA
<213> ORGANISM: Homo sapiens

<400> SEQUENCE: 299
tcacagtgcc                                                             10

<210> SEQ ID NO 300
<211> LENGTH: 10
<212> TYPE: DNA
<213> ORGANISM: Homo sapiens

<400> SEQUENCE: 300
tcaccggtca                                                             10

<210> SEQ ID NO 301
<211> LENGTH: 10
<212> TYPE: DNA

<213> ORGANISM: Homo sapiens

<400> SEQUENCE: 301
tcagagcgct                                                           10

<210> SEQ ID NO 302
<211> LENGTH: 10
<212> TYPE: DNA
<213> ORGANISM: Homo sapiens

<400> SEQUENCE: 302
tcagctgcaa                                                           10

<210> SEQ ID NO 303
<211> LENGTH: 10
<212> TYPE: DNA
<213> ORGANISM: Homo sapiens

<400> SEQUENCE: 303
tcagctgcaa                                                           10

<210> SEQ ID NO 304
<211> LENGTH: 10
<212> TYPE: DNA
<213> ORGANISM: Homo sapiens

<400> SEQUENCE: 304
tcggagctgt                                                           10

<210> SEQ ID NO 305
<211> LENGTH: 10
<212> TYPE: DNA
<213> ORGANISM: Homo sapiens

<400> SEQUENCE: 305
tctgaattat                                                           10

<210> SEQ ID NO 306
<211> LENGTH: 10
<212> TYPE: DNA
<213> ORGANISM: Homo sapiens

<400> SEQUENCE: 306
tgactaattg                                                           10

<210> SEQ ID NO 307
<211> LENGTH: 10
<212> TYPE: DNA
<213> ORGANISM: Homo sapiens

<400> SEQUENCE: 307
tgagtgacag                                                           10

<210> SEQ ID NO 308
<211> LENGTH: 10
<212> TYPE: DNA
<213> ORGANISM: Homo sapiens

<400> SEQUENCE: 308
tgagtgacag                                                           10

<210> SEQ ID NO 309
<211> LENGTH: 10
<212> TYPE: DNA

```
<213> ORGANISM: Homo sapiens

<400> SEQUENCE: 309
tgatctctgt                                                          10

<210> SEQ ID NO 310
<211> LENGTH: 10
<212> TYPE: DNA
<213> ORGANISM: Homo sapiens

<400> SEQUENCE: 310
tgcagcacga                                                          10

<210> SEQ ID NO 311
<211> LENGTH: 10
<212> TYPE: DNA
<213> ORGANISM: Homo sapiens

<400> SEQUENCE: 311
tgcagcgcct                                                          10

<210> SEQ ID NO 312
<211> LENGTH: 10
<212> TYPE: DNA
<213> ORGANISM: Homo sapiens

<400> SEQUENCE: 312
tgccgcccgc                                                          10

<210> SEQ ID NO 313
<211> LENGTH: 10
<212> TYPE: DNA
<213> ORGANISM: Homo sapiens

<400> SEQUENCE: 313
tgctcctacc                                                          10

<210> SEQ ID NO 314
<211> LENGTH: 10
<212> TYPE: DNA
<213> ORGANISM: Homo sapiens

<400> SEQUENCE: 314
tgctcctacc                                                          10

<210> SEQ ID NO 315
<211> LENGTH: 10
<212> TYPE: DNA
<213> ORGANISM: Homo sapiens

<400> SEQUENCE: 315
tggccatctg                                                          10

<210> SEQ ID NO 316
<211> LENGTH: 10
<212> TYPE: DNA
<213> ORGANISM: Homo sapiens

<400> SEQUENCE: 316
tggcgcgtgt                                                          10

<210> SEQ ID NO 317
<211> LENGTH: 10
<212> TYPE: DNA
```

<210> SEQ ID NO 317
<211> LENGTH: 10
<212> TYPE: DNA
<213> ORGANISM: Homo sapiens

<400> SEQUENCE: 317
tggctactta                                                          10

<210> SEQ ID NO 318
<211> LENGTH: 10
<212> TYPE: DNA
<213> ORGANISM: Homo sapiens

<400> SEQUENCE: 318
tggggagagg                                                          10

<210> SEQ ID NO 319
<211> LENGTH: 10
<212> TYPE: DNA
<213> ORGANISM: Homo sapiens

<400> SEQUENCE: 319
ttaacccctc                                                          10

<210> SEQ ID NO 320
<211> LENGTH: 10
<212> TYPE: DNA
<213> ORGANISM: Homo sapiens

<400> SEQUENCE: 320
ttatggtgtg                                                          10

<210> SEQ ID NO 321
<211> LENGTH: 10
<212> TYPE: DNA
<213> ORGANISM: Homo sapiens

<400> SEQUENCE: 321
ttccactaac                                                          10

<210> SEQ ID NO 322
<211> LENGTH: 10
<212> TYPE: DNA
<213> ORGANISM: Homo sapiens

<400> SEQUENCE: 322
ttccgcgttc                                                          10

<210> SEQ ID NO 323
<211> LENGTH: 10
<212> TYPE: DNA
<213> ORGANISM: Homo sapiens

<400> SEQUENCE: 323
ttctggtgcg                                                          10

<210> SEQ ID NO 324
<211> LENGTH: 10
<212> TYPE: DNA
<213> ORGANISM: Homo sapiens

<400> SEQUENCE: 324
ttctgtagcc                                                          10

<210> SEQ ID NO 325
<211> LENGTH: 10
<212> TYPE: DNA

<213> ORGANISM: Homo sapiens

<400> SEQUENCE: 325
ttggacctgg                                                            10

<210> SEQ ID NO 326
<211> LENGTH: 10
<212> TYPE: DNA
<213> ORGANISM: Homo sapiens

<400> SEQUENCE: 326
ttggggtttc                                                            10

<210> SEQ ID NO 327
<211> LENGTH: 10
<212> TYPE: DNA
<213> ORGANISM: Homo sapiens

<400> SEQUENCE: 327
tttaacggcc                                                            10

<210> SEQ ID NO 328
<211> LENGTH: 10
<212> TYPE: DNA
<213> ORGANISM: Homo sapiens

<400> SEQUENCE: 328
tttcctctca                                                            10

<210> SEQ ID NO 329
<211> LENGTH: 10
<212> TYPE: DNA
<213> ORGANISM: Homo sapiens

<400> SEQUENCE: 329
tttcctctca                                                            10

<210> SEQ ID NO 330
<211> LENGTH: 10
<212> TYPE: DNA
<213> ORGANISM: Homo sapiens

<400> SEQUENCE: 330
tttctcgtcg                                                            10

<210> SEQ ID NO 331
<211> LENGTH: 10
<212> TYPE: DNA
<213> ORGANISM: Homo sapiens

<400> SEQUENCE: 331
tttggtttca                                                            10

<210> SEQ ID NO 332
<211> LENGTH: 10
<212> TYPE: DNA
<213> ORGANISM: Homo sapiens

<400> SEQUENCE: 332
ttttctgcat                                                            10

<210> SEQ ID NO 333
<211> LENGTH: 10
<212> TYPE: DNA

```
<213> ORGANISM: Homo sapiens

<400> SEQUENCE: 333
ttttctgcat                                                              10

<210> SEQ ID NO 334
<211> LENGTH: 10
<212> TYPE: DNA
<213> ORGANISM: Homo sapiens

<400> SEQUENCE: 334
tttttactga                                                              10
```

METHODS FOR DETECTION OF COLORECTAL CANCER

BACKGROUND OF THE INVENTION

1. Technical Field of the Invention

The invention relates to the early detection of colorectal adenoma and carcinoma. In particular it relates to the detection of secreted or cell surface markers in easily collectible bodily samples.

2. Background of the Art

Colorectal cancer is the second leading cause of cancer death in the United States, with ~130,000 patients diagnosed each year and ~50,000 ultimately succumbing to the disease (1). Most colorectal cancers develop slowly, beginning as small benign colorectal adenomas which progress over several decades to larger and more dysplastic lesions which eventually become malignant. This gradual progression provides multiple opportunities for prevention and intervention. Indeed, benign adenomas can be detected and removed by simple colonoscopy and polypectomy, precluding the need for radical surgical and adjuvant treatments. It is therefore believed that early detection and removal of these benign neoplasms provides the best hope for minimizing morbidity and mortality from colorectal cancer. Various screening methods for detecting early colorectal tumors are available, such as fecal occult blood testing, sigmoidoscopy, and colonoscopy (reviewed in 2). However, none of these methods are optimal, and new approaches are needed.

BRIEF SUMMARY OF THE INVENTION

In a first embodiment a method is provided for detection of colorectal adenoma and carcinoma. An mRNA sample is isolated from feces of a subject. Renal dipeptidase mRNA in said mRNA sample is detected. The amount of renal dipeptidase mRNA in said mRNA sample is compared to amounts of renal dipeptidase mRNA in normal subjects. An elevated amount of renal dipeptidase mRNA in said mRNA sample is an indicator of colorectal adenoma or carcinoma in the subject.

According to another embodiment of the invention a method is provided for detection of colorectal adenoma or carcinoma. Epithelial cells are isolated from blood of a subject. An mRNA sample is isolated from the epithelial cells. Renal dipeptidase mRNA in said mRNA sample is detected. The amount of renal dipeptidase mRNA in said mRNA sample is compared to amounts of renal dipeptidase mRNA in normal subjects. An elevated amount of renal dipeptidase mRNA in said mRNA sample is an indicator of colorectal adenoma or carcinoma in the subject.

A third embodiment of the invention provides a method for detection of colorectal adenoma or carcinoma. Blood of a subject is contacted with a renal dipeptidase substrate. Activity of renal dipeptidase in said blood is determined by detection of increased reaction product or decreased renal dipeptidase substrate. The amount of activity of renal dipeptidase in blood of the subject is compared to that in normal subjects. An elevated amount of activity of renal dipeptidase in the blood of the subject is an indicator of colorectal adenoma or carcinoma in the subject.

According to another embodiment of the invention a method for detection of colorectal adenoma or carcinoma is provided. Feces of a subject is contacted with a renal dipeptidase substrate. Activity of renal dipeptidase in said feces is determined by detection of increased reaction product or decreased renal dipeptidase substrate. The amount of activity of renal dipeptidase in feces of the subject is compared to that in normal subjects, wherein an elevated amount of activity of renal dipeptidase in the feces of the subject is an indicator of colorectal adenoma or carcinoma in the subject.

Another embodiment of the invention provides a method for detection of colorectal adenoma or carcinoma. An antibody is administered to a subject. The antibody specifically binds to renal dipeptidase and is labeled with a moiety which is detectable from outside of the subject. The moiety in the subject is detected from outside of the subject. An area of localization of the moiety within the subject but outside the proximal tubules of the kidney identifies colorectal adenoma or carcinoma.

Another method is also provided for detection of colorectal adenoma or carcinoma. An inhibitor of renal dipeptidase is administered to a subject. The inhibitor is labeled with a moiety which is detectable from outside of the subject. The moiety in the subject is detected from outside of the subject. An area of localization of the moiety within the subject but outside the proximal tubules of the kidney identifies colorectal adenoma or carcinoma.

According to yet another method for detection of colorectal adenoma or carcinoma, a substrate for renal dipeptidase is administered to a subject. The substrate is labeled with a detectable moiety. Feces are isolated from the subject. Renal dipeptidase reaction product or renal dipeptidase substrate with the detecable moiety is detected in the feces. An increased reaction product or decreased reaction substrate in the feces indicates colorectal adenoma or carcinoma in the subject.

Still another method for detection of colorectal adenoma or carcinoma is provided by the present invention. A substrate for renal dipeptidase is administered to a subject. The substrate is labeled with a detectable moiety. Blood from the subject is subsequently isolated. Renal dipeptidase reaction product or renal dipeptidase substrate with the detecable moiety is detected in the blood. An increased product or decreased substrate in the blood indicates colorectal adenoma or carcinoma in the subject.

Still another embodiment of the invention is a method for detection of colorectal adenoma or carcinoma. Renal dipeptidase in blood of a subject is detected and compared to the amount of renal dipeptidase in normal subjects. An elevated amount of renal dipeptidase in the blood of the subject is an indicator of colorectal adenoma or carcinoma in the subject.

Still another embodiment of the invention is a method for detection of colorectal adenoma or carcinoma. Renal dipeptidase in feces of a subject is detected and compared to the amount of renal dipeptidase in normal subjects. An elevated amount of renal dipeptidase in the feces of the subject is an indicator of colorectal adenoma or carcinoma in the subject.

Yet another embodiment of the invention is a method for detection of colorectal adenoma or carcinoma. An mRNA sample is isolated from feces of a subject. Macrophage inhibitory cytokine mRNA is detected in the mRNA sample. The amount of macrophage inhibitory cytokine mRNA in said mRNA sample is compared to amounts of macrophage inhibitory cytokine mRNA in normal subjects. An elevated amount of macrophage inhibitory cytokine mRNA in said mRNA sample is an indicator of colorectal adenoma or carcinoma in the subject.

Another embodiment of the invention is a method for detection of colorectal adenoma or carcinoma. Epithelial cells are isolated from blood of a subject. An mRNA sample is isolated from the epithelial cells. Macrophage inhibitory cytokine mRNA is detected in said mRNA sample. The amount of macrophage inhibitory cytokine mRNA in said mRNA sample is compared to amounts of macrophage inhibitory cytokine mRNA in normal subjects. An elevated amount of macrophage inhibitory cytokine mRNA in said mRNA sample is an indicator of colorectal adenoma or carcinoma in the subject.

Still another embodiment of the invention is a method for detection of colorectal adenoma or carcinoma. Macrophage inhibitory cytokine in blood of a subject is detected and compared to the amount of macrophage inhibitory cytokine in normal subjects. An elevated amount of macrophage inhibitory cytokine in the blood of the subject is an indicator of colorectal adenoma or carcinoma in the subject.

Still another embodiment of the invention is a method for detection of colorectal adenoma or carcinoma. Macrophage inhibitory cytokine in feces of a subject is detected and compared to the amount of macrophage inhibitory cytokine in normal subjects. An elevated amount of macrophage inhibitory cytokine in the feces of the subject is an indicator of colorectal adenoma or carcinoma in the subject.

BRIEF DESCRIPTION OF THE DRAWINGS

FIG. 1.A, Distribution of the fold changes of differentially expressed transcript tags. Transcripts in which the significance criterion was met (p<0.05, a total of 957 tags) in the comparisons between normal and adenoma or normal and cancer are plotted in the figure. The ratios of adenoma to normal and cancer to normal were plotted on a log scale. The shaded box in (FIG. 1.A) and enlarged in (FIG. 1.B) encloses the transcript tags detailed in Table 3. The two unlabeled dots correspond to tags whose differential expression could not be confirmed by quantitative PCR suggesting that the tags were derived from different transcripts than the ones indicated in Table 3.

FIG. 5A-FIG. 5E. In-situ hybridization analyses of elevated genes. Genes examined were REGA (FIG. 5A), TGFBI (FIG. 5B), LYS (FIG. 5C), RDP (FIG. 5D), and MIC-1 (FIG. 5E). Positive cells appear red, arrows point to clusters of malignant epithelial cells, and arrow heads point to macrophages.

FIG. 8. Substrates of renal dipeptidase are shown.

FIG. 9 shows the difference in activity of renal dipeptidase found in adenomas, cancer, and metastases compared to normal colonic tissue.

DETAILED DESCRIPTION OF THE INVENTION

It is a finding of the present invention that particular genes are aberrantly and consistently expressed in both adenomas and carcinomas of the colon. Products of such genes provide cellular and serum markers for colorectal neoplasia. The ideal tumor marker would be expected to have several characteristics. First, it should be expressed at high levels in tumors and at greatly reduced levels in normal tissues. Second the elevated expression should occur early and remain elevated during the neoplastic process. Third, such a marker should be elevated in the majority of clinical samples. Fourth, the marker should be cell surface or secreted to facilitate its detection. We have identified several genes that appear to meet all of these criteria and may therefore be especially useful as diagnostic tools for the early detection of colorectal neoplasia, even of presymptomatic colorectal neoplasia. Any of the markers identified in Tables 3 and 5 can be used, particularly Renal Dipeptidase and Macrophage Inhibitory Cytokine.

Serum markers can be found and detected in whole blood, serum, plasma, or fractions thereof. These are collectively referred to as "blood" herein. Markers can also be found in stool. Samples for testing can be feces or processed or fractionated feces. All such samples are referred to herein as "feces."

Figure 6:
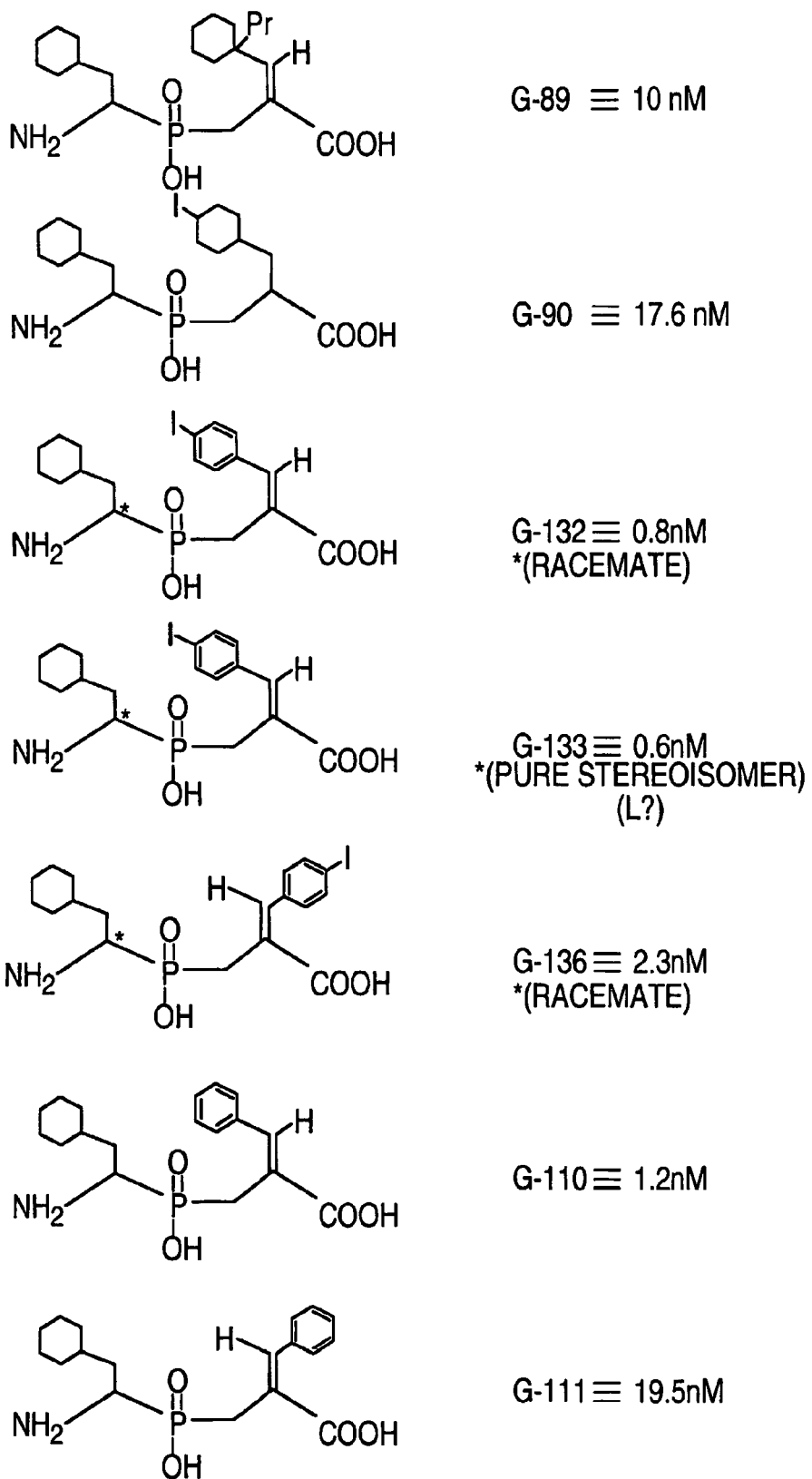
FIG. 6. Inhibitors of renal dipeptidase demonstrate inhibition constants ranging from 0.6 nM to 19.5 nM.
Figure 7:
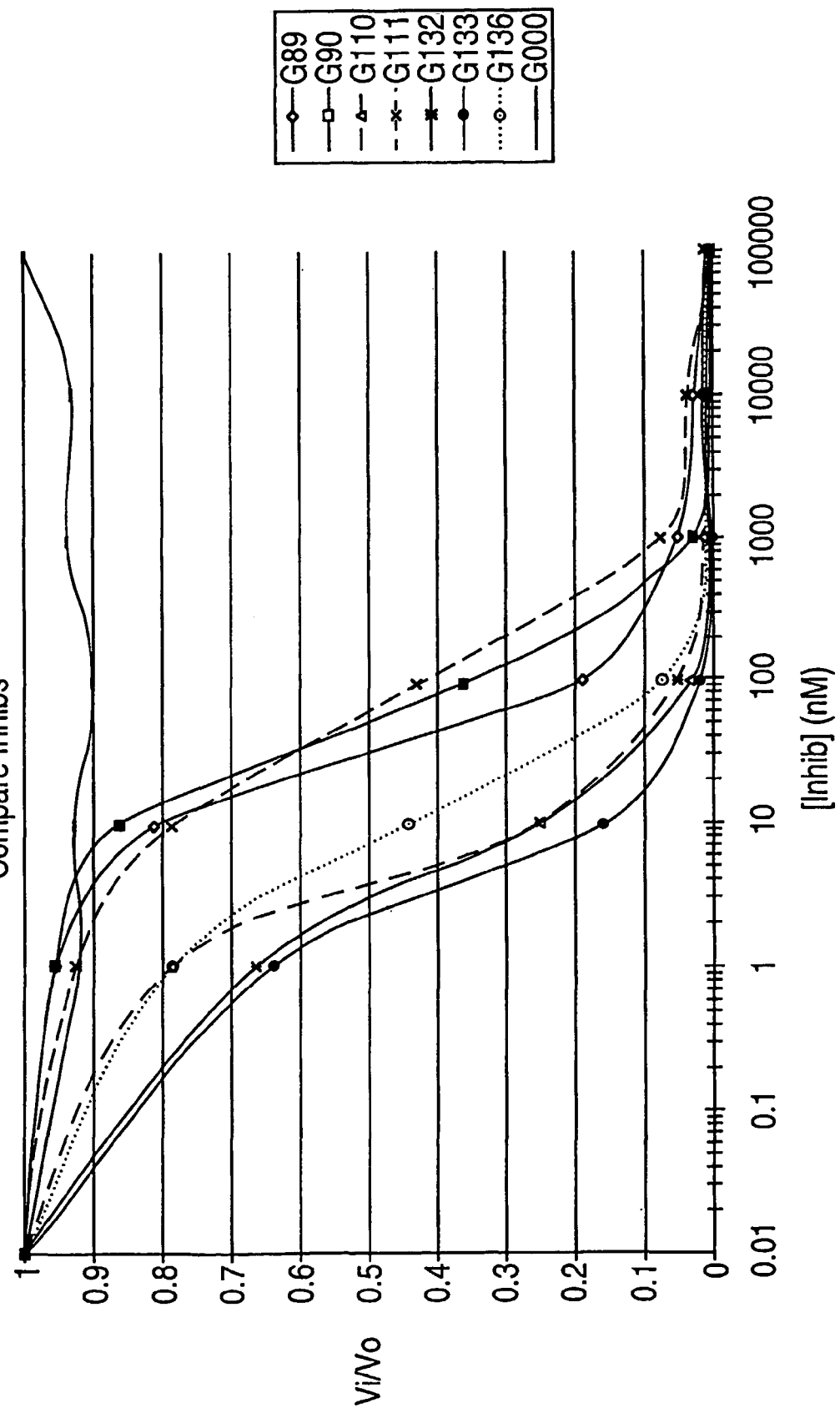
FIG. 7. A comparison of the inhibitors shown in FIG. 6. compares the inhibition rate as a function of concentration of inhibitor.

Inhibitors of markers which are enzymes, such as Renal Dipeptidase, can be used as affinity reagents for labeling the marker. Preferably the inhibitors are those which bind irreversibly. Alternatively they are ones which bind and release, but release at a slow rate. Inhibitors with suitably slow release rates are those which have a binding half-life of greater than 30 minutes, or 1, 2, 3, 5, 8, or 10 hours. Many inhibitors of Renal Dipeptidase are known, including the commercially available Cilastatin, and phosphinic acid inhibitors. See Parsons et al., "A new class of potent, slowly reversibly dehydropeptidase inhibitors," *Biochemistry International*, vol. 23, pp. 1107-1115, 1991. Inhibitors which covalently bind to and/or modify Renal Dipeptidase are also known and can be used. See Wu and Mobashery, "Targeting renal dipeptidase (dehydropeptidase I) for inactivation by mechanism-based inactivators," *J. Med. Chem.*, vol. 34, pp. 1914-1916, 1991. Some inhibitors mimic transition states between substrates and product. Some useful inhibitors are shown in FIG. 6. These include inhibitors having halogen substitutions. Such inhibitors can be readily made using radioactive halogens for ready labeling of renal dipeptidase and easy detection. Similar inhibitors of other enzymes are also known in the art and can be used. Inhibitors can be labeled using any detectable moiety known in the art, including but not limited to fluors and radioactive atoms.

RNA for any of the markers can be detected using any of the known techniques in the art. Preferably an amplification step will be used, because the amount of RNA for the marker is expected to be very small from the sources contemplated.

Suitable techniques include RT-PCR, hybridization of copy mRNA (cRNA) to an array of nucleic acid probes, and Northern blotting.

Protein forms of the markers can be detected using any techniques known in the art. These include activity assays, immunological assays, binding to specific ligands, etc. Particularly suitable assays for Renal Dipeptidase include using L-L amino acid dipeptide substrates and L-D amino acid dipeptide substrates. Substrates which can be used for assaying renal dipeptidase are shown in FIG. 8, and include the generic structures for dipeptides and dehydrodipeptides. ϵ (DNP)-L-Lysine-D-Amp can also be used as a substrate, yielding a colored product. Substrates for other enzymes can be used similarly to assess the presence of the tumor marker enzyme in the body or in a body sample. Such substrates can be labeled with detectable moieties, including but not limited to fluors and radioactive atoms. One particularly useful labeling scheme employs a substrate which is labeled with two moieties on opposite sides of the substrate cleavage site. One of the moieties is fluorescent and one of the moieties is a quencher. When the two moieties are close, as in an intact substrate, the fluorescence of the fluorescent moiety is quenched. Upon cleavage the quenching is released and an increase in fluorescence is observed.

As mentioned above, inhibitors can also be labeled and used for detecting suitable markers. In addition, antibodies can be used to label protein forms of the markers. The antibodies can be labeled as is known in the art. Suitable radioactive atoms for use in labeling inhibitors, substrates, and antibodies include In-111, I-123, Tc-99m, Re-186, Re-188, Ga-67, Ga-68, Tl-201, Fe-52, Pb-203, Co-58, Cu-64, I-124, I-125, I-131, At-210, Br-76, Br-77, and F-18 and others known in the art for such purposes. Contrast enhancement agents can also be attached to the substrates, inhibitors, or antibodies. Such agents include gadolinium. Moreover, imaging techniques can be used to detect such labels within the body. An example of an imaging technique which can be used is spiral computer tomography. For this technique, the detecting agent, such as inhibitor or antibody can be linked to a contrast enhancing agent. Other detection means that can be used include gamma cameras, magnetic resonance imaging, planar scintigraphic imaging, SPECT imaging, PET imaging, and ultrasound imaging. Thus markers can be detected both in situ in the body or in vitro in an isolated body sample.

Epithelial cells can be isolated from blood or other tissue samples to enrich for the markers or their mRNAs. Epithelial cells can be isolated, inter alia, by immunoaffinity techniques. Such a technique is described in more detail below.

Substrates of enzymic markers can be administered to subjects and the reaction products measured in body samples. Inhibitors can be administered to subjects and the subject can be imaged to detect the inhibitor bound to the marker. Such markers are preferably those which are not secreted proteins, but rather are those which are anchored to a tumor. Typical modes of administration of such agents can be any which is suitable, including but not limited to per os, intravenous, intramuscular, intraarterial, subdermal, transdermal, and rectal.

A high background of certain markers may obscure detection of increased expression. In such a situation, one can use tumor-specific glycoforms as a means of distinguishing between the background marker and the marker that is due to the tumor. Tumor-specific glycoforms of Renal Dipeptidase and MIC-1 bind to LPHA, an L lectin from Phaseolus vulgaris hemagglutinin, and thus can be distinguished on that basis. Other lectins such as with similar specificity for tumor-specific glycoforms, such as Sambucus Nigra Lectin isolated from Sambucus nigra (elderberry) bark can be used as well.

Normal subjects are used as a comparison to the test subjects to determine whether the amounts of markers observed in the feces or blood are elevated. Preferably the normal subjects have been confirmed as tumor-free by colonoscopy. More preferably several samples are pooled or their individual values are averaged to arrive at a normal value.

Some of the most highly overexpressed genes found in colorectal adenomas and colorectal cancers are discussed below. Regenerating Islet Derived Pancreatic Stone Protein, encoded by the REGA gene, is a secreted polypeptide first found in pancreatic precipitates and stones from patients suffering from chronic pancreatitis (7). The cDNA encoding this protein was isolated from a random screen of genes highly expressed in a regenerating-islet derived cDNA library (8) and subsequently shown to be elevated in colorectal cancers (9). More recently, REGA was isolated in a hybridization-based screen for genes elevated in colorectal cancers and shown to be elevated in many colorectal adenocarcinomas (10). Consistent with these published observations, we observed a strong elevation in expression of REGA in unpurified tumors, and a similar elevation in one purified tumor. In situ hybridization experiments demonstrated REGA to be strongly expressed in the epithelial cells of the tumors, with no expression evident in the stroma (FIG. 5A).

TGFB-induced gene (TGFBI) encodes a small polypeptide of unknown function initially isolated through a differential display screen for genes induced in response to treatment with TGF β (11). The protein is expressed in the keratinocytes of the cornea (12) and, interestingly, germline mutations of this gene cause familial corneal dystrophies (13). TGFBI was previously shown to be among the most significantly elevated genes in colorectal cancers (4), and our new data show that it is expressed at high levels in adenomas as well. Quantitative PCR results demonstrated strong elevation both in unpurified tumors and purified tumor epithelial cells. Accordingly, in situ hybridization experiments revealed TGFBI to be expressed in many cell types, in both the stromal and epithelial compartments (FIG. 5B).

Lysozyme (LYS, 1,4-β-N-acetylmuramidase, EC 3.2.1.17) is an enzyme with bacteriolytic activity (14) capable of cleaving β-1,4 glycosidic bonds found in the cell walls of gram-positive bacteria. The enzyme is expressed in the secretory granules of monocytes, macrophages and leukocytes, as well as in the Paneth cells of the gastrointestinal tract. Fecal lysozyme levels are dramatically elevated in patients with inflammatory bowel disease (15, 16), and serum lysozyme activity is significantly elevated in patients with sarcoidosis (17), both of which are diseases characterized by aberrant chronic inflammation. Furthermore, lysozyme immunoreactivity has been observed in the epithelial cells of both adenomas and carcinomas of the large intestine (18). In our study, the degree of elevation of expression of LYS varied from 4-fold to 55-fold in the unpurified samples. In contrast, the degree of elevation of expression of LYS observed in purified epithelial cells was only 2-5 fold. This suggested that a substantial portion of the expression for this gene in the tumors could have been derived from non-epithelial cells. Consistent with this hypothesis, in situ hybridization experiments revealed that the majority of LYS mRNA was present in a stromal component that appeared to be macrophages (FIG. 5C). The expression of LYS in the macrophage compartment of colorectal tumors was also supported by its high representation in a SAGE library constructed from hematopoietic cells (CD45+, CD64+, CD14+) purified from colorectal tumors (602 LYS tags/56,643 total tags) (6).

One interesting gene identified in the current study is renal dipeptidase (RDP). RDP is a GPI-anchored enzyme whose major site of expression is the epithelial cells of the proximal tubules of the kidney (reviewed in (19)). The enzyme has been extensively analyzed with respect to its catalytic mechanism and inhibition kinetics by a variety of synthetic inhibitors. RDP is unique among the dipeptidases in that it can cleave amide bonds in which the C-terminal partner is a D amino acid, providing excellent opportunity for the development of specific probes for its detection in vivo. Quantitative PCR revealed RDP to be markedly elevated in both unpurified and purified tumor epithelial cells, and in situ hybridization experiments showed that RDP was exclusively localized to epithelial cells of colorectal tumors (FIG. 5D).

Macrophage Inhibitory Cytokine (MIC-1) is a small polypeptide of 16 kDa first isolated from a differential screen for genes that were induced upon macrophage activation (20). Concurrently, it was identified in the IMAGE database by a search for molecules homologous to the Bone Morphogenic Protein/TGF β family of growth and differentiation factors (21). In addition to being highly expressed in activated macrophages, MIC-1 has been noted to be highly expressed in placenta and the epithelial cells of normal prostate. In the current study, we found MIC-1 expression to be elevated between 7 and 133 fold in the unpurified tumors. As observed for LYS, the purified tumor cells demonstrated significant but less elevation of expression of MIC-1 (5 to 7-fold) indirectly implicating stromal expression to be partly responsible for the dramatic elevation seen in some tumors. Consistent with this hypothesis, in situ hybridization experiments revealed expression in both the epithelium of the tumor, and in a cell type resembling infiltrating macrophages (FIG. 5E).

EXAMPLES

Example 1

SAGE

In an effort to identify potential molecular markers of early colorectal tumors, we have here analyzed gene expression in benign and malignant colorectal tumors in an unbiased and comprehensive fashion. We used SAGE to analyze global gene expression in normal, benign and malignant colorectal tissue. SAGE is a gene expression profiling method that associates individual mRNA transcripts with 15-base tags derived from specific positions near their 3' termini (3). The abundance of each tag provides a quantitative measure of the transcript level present within the mRNA population studied. SAGE is not dependent on pre-existing databases of expressed genes, and therefore provides an unbiased view of gene expression profiles. For the current study, SAGE libraries derived from two samples of normal colonic epithelium, two colorectal adenomas, and two colorectal cancers were analyzed. These libraries contained a combined total of 290,394 transcript tags representing 21,343 different transcripts (Table 1).

TABLES 1

Summary of SAGE data

| SAGE Library | Total number of tags observed | Number of different transcripts observed* |
|---|---|---|
| Normal Colorectal Epithelium | | |
| NC-1 | 49,610 | 9,359 |
| NC-2 | 48,479 | 9,610 |
| Adenomas | | |
| Ad-A | 52,573 | 11,167 |
| Ad-B | 42,661 | 9,483 |
| Cancers | | |
| Tu-98 | 41,371 | 9,780 |
| Tu-102 | 55,700 | 11,039 |
| Total | 290,394 | 21,343 |

*To minimize the effect of potential sequencing errors, only tags observed more than once in a given SAGE library were counted to give a conservative estimate of the minimum number of different transcripts analyzed.

Two comparisons were performed, one between the adenoma and normal samples, and one between the cancer and normal samples. These comparisons revealed 957 transcript tags that were differentially expressed more than 2-fold between normal and tumor tissue (Table 2). A comparison of the fold change in adenomas versus cancers revealed that many transcripts were similarly elevated or repressed in both adenomas and cancers although the magnitude often varied (FIG. 1A). Indeed the majority (79%) of comparisons were in quadrants of the plot indicative of concordant elevation.

TABLE 2

Differentially expressed transcripts in benign and malignant tumor colorectal tissue

| Fold change in expression | Elevated in adenomas[a] | Elevated in cancers[a] | Elevated in both adenomas and cancer[a] | Repressed in adenomas[b] | Repressed in cancers[b] | Repressed in both adenomas and cancers[b] | Total transcripts differentially expressed |
|---|---|---|---|---|---|---|---|
| 2 | 346 | 170 | 50 | 313 | 380 | 192 | 957 |
| 4 | 263 | 119 | 23 | 225 | 270 | 117 | 735 |
| 10 | 160 | 79 | 10 | 134 | 157 | 58 | 462 |
| 20 | 49 | 40 | 9 | 72 | 52 | 23 | 181 |

[a]Elevated transcripts showed a significantly different ($P < 0.05$) tag count between normal and tumor tissue, were expressed in both tumor tissues analyzed, and had an expression level that was higher in the tumors than in the normals by the fold indicated in column one. For the purposes of calculation, 0.5 was substituted for the denominator when no tags were detected in the normal samples.
[b]Repressed transcripts showed a significantly different ($P < 0.05$) tag count between normal and tumor tissue, were expressed in both normal tissues analyzed and had an expression level that was lower in the tumors than in the normals by the fold indicated in column one.

From both practical and biological perspectives, those changes showing the greatest magnitude were deemed the most interesting. In this regard, 49 tags were identified to be elevated by ≧20-fold in the adenomas and 40 were elevated by ≧20-fold in the cancers (Table 2). Conversely, there were 72 transcripts that were decreased by ≧20-fold in adenomas and 52 decreased by ≧20-fold in the cancers (Table 2).

There were nine transcripts that were elevated by ≧20-fold in both adenomas and cancers (FIG. 1B and Table 3) and 23 that were repressed by ≧20-fold (Table 4). Other elevated and repressed transcripts are shown in Table 5. Tags for the transcripts shown in Table 5 are listed as SEQ ID NO: 33-334. We were especially interested in genes whose products were predicted to be secreted or displayed on the cell surface, as these would be particularly suitable for the development of serologic or imaging tests for presymptomatic neoplasia, respectively. We were able to identify six such genes (TGFBI, LYS, RDP, MIC-1, REGA and DEHL) from among those whose transcript tags were elevated in both adenoma and carcinoma SAGE libraries.

TABLE 3

Transcripts most elevated in adenomas and cancers[a]

| Tag Sequence | Normal | | Adenomas | | Cancers | | Transcript name |
| | NC-1 | NC-2 | AD-A1 | AD-B2 | Tu-98 | Tu-102 | |
| --- | --- | --- | --- | --- | --- | --- | --- |
| ATGTAAAAAA | 0 | 0 | 26 | 32 | 2 | 12 | Lysozyme (LYS) |
| TAATTTTTGC | 0 | 1 | 99 | 12 | 20 | 37 | Differentially Expressed in Hematopoietic Lineages (DEHL) |
| GTGTGTTTGT | 0 | 0 | 17 | 29 | 17 | 15 | Transforming Growth Factor, Beta-Induced (TGFBI) |
| GTGCTCATTC | 0 | 0 | 13 | 7 | 2 | 10 | Macrophage Inhibitory Cytokine, 1 (MIC-1) |
| TTCCAGCTGC | 0 | 0 | 7 | 6 | 2 | 9 | Adaptor-related Protein Complex 2, alpha 2 subunit[b] |
| ACCATTGGAT | 0 | 0 | 3 | 10 | 3 | 9 | Interferon Induced Transmembrane Protein 1 (9-27)[b] |
| TTTCCACTAA | 0 | 0 | 8 | 4 | 4 | 6 | Regenerating Islet-Derived 1 alpha (REGA) |
| CAAGGACCAG | 0 | 0 | 5 | 6 | 10 | 12 | Renal Dipeptidase (RDP) |
| AGGACCATCG | 0 | 0 | 8 | 2 | 1 | 18 | Defensin, Alpha 5, Paneth cell-specific[c] |

[a]These tags (SEQ ID NOS: 1-9) displayed at least twenty fold elevation in both neoplastic states. The numbers given are the raw tag counts for each tag observed in each library. Transcript name provides a description of matching UniGene cluster (Build Mar. 13, 2001). Rows shown in bold are genes confirmed by quantitative PCR to be differentially expressed.

[b]Differential expression could not be confirmed by quantitative PCR suggesting that the tag was derived from a different transcript than the one indicated.

[c]Not tested.

TABLE 4

Transcripts most repressed in adenomas and cancers[a]

| Tag Sequence | Normal | | Adenoma | | Cancer | | UNI ID | Transcript name |
| | NC-1 | NC2 | AD-A1 | AD-B | Tu-981 | Tu-102 | | |
| --- | --- | --- | --- | --- | --- | --- | --- | --- |
| GTCATCACCA | 35 | 22 | 0 | 0 | 0 | 0 | 32966 | Guanylate Cyclase Activator 2B |
| CCTTCAAATC | 29 | 17 | 0 | 0 | 1 | 0 | 23118 | Carbonic Anhydrase I |
| TCTGAATTAT | 24 | 16 | 0 | 0 | 1 | 0 | 50964 | Carcinoembryonic Antigen-Related Cell Adhesion Molecule 1 |
| TTATGGTGTG | 11 | 17 | 0 | 0 | 0 | 0 | 271499 | ESTs |
| CTGGCAAAGG | 14 | 22 | 1 | 0 | 0 | 0 | 72789 | hypothetical protein FLJ20217 |
| AGGTGACTGG | 10 | 14 | 0 | 0 | 0 | 0 | | No Match |
| CTTATGGTCC | 36 | 11 | 0 | 1 | 1 | 0 | 179608 | Retinol Dehydrogenase Homolog |
| ATGATGGCAC | 12 | 32 | 1 | 0 | 1 | 0 | 84072 | Transmembrane 4 Superfamily Member 3 |
| GTCCGAGTGC | 17 | 3 | 0 | 0 | 0 | 0 | 3337 | Transmembrane 4 Superfamily Member 1 |
| ATTTCAAGAT | 35 | 21 | 0 | 2 | 1 | 0 | 155097 | Carbonic Anhydrase II (CA2) |
| CAAGAGTTTC | 14 | 2 | 0 | 0 | 0 | 0 | 183617 | ESTs |
| GCCATCCTCC | 9 | 13 | 0 | 1 | 0 | 0 | | No Match |
| ACCCAACTGC | 12 | 3 | 0 | 0 | 0 | 0 | 232604 | *Homo sapiens* cDNA: FLJ22675 fis, clone HSI10553 |
| GCCCACGTCA | 7 | 8 | 0 | 0 | 0 | 0 | | No Match |
| TTTGGTTTCA | 2 | 13 | 0 | 0 | 0 | 0 | | No Match |
| CTCAGAACTT | 18 | 3 | 1 | 0 | 0 | 0 | 194710 | N-acetylglucosaminyl transferase 3, mucin type |
| CCAACACCAG | 9 | 19 | 1 | 0 | 0 | 1 | 181165 | Eukaryotic Translation Elongation Factor 1 Alpha 1 |
| GCCACATACT | 3 | 9 | 0 | 0 | 0 | 0 | 4984 | KIAA0828 protein |
| GTATTGGGGC | 5 | 7 | 0 | 0 | 0 | 0 | | No Match |
| CCGGCTTGAG | 7 | 4 | 0 | 0 | 0 | 0 | 2722 | Inositol 1,4,5-trisphosphate 3-Kinase A |
| GATATGTAAA | 1 | 10 | 0 | 0 | 0 | 0 | 227059 | Chloride Channel, Calcium Activated, Family Member 4 |
| CATAGGTTTA | 66 | 39 | 4 | 1 | 5 | 0 | 1650 | Solute Carrier Family 26, member 3 (DRA) |
| GTCCTGAACA | 7 | 3 | 0 | 0 | 0 | 0 | 78546 | ATPase, Ca++ Transporting, Plasma Membrane 1 |

[a]These tags (SEQ ID NOS: 10-32) displayed at least twenty fold decrease in both neoplastic states. The numbers given are the raw tag counts for each tag observed in each library. Transcript name provides a description of matching UniGene cluster (Build Mar. 13, 2001). Rows shown in bold are genes that were tested and confirmed by quantitative PCR to be differentially expressed.

SAGE. For the initial SAGE[3] of benign tumors, fresh adenomas were obtained from surgical specimens derived from FAP patients. Adenomas from FAP patients were employed because of the ready availability of small lesions and the certainty of inactivation of the APC pathway which initiates the formation of the majority of sporadic tumors. After histopathological verification of the neoplastic nature of the lesion (>70% neoplastic cells), total RNA was isolated by solubilizing the tissue in RNAgents Lysis Buffer (Promega, Madison, Wis.) followed by ultracentrifugation over a cesium chloride gradient. mRNA selection was performed from the purified total RNA using oligo(dT) cellulose (Life Technologies, Gaithersburg, Md.). Two adenoma SAGE libraries were prepared as described (3, 4) and sequenced to a total depth of over 90,000 transcript tags. For SAGE of normal and malignant tissues, four previously described normal (NC-1 and NC-2) and primary cancer (Tu-98 and Tu-102) SAGE libraries were employed (4). In collaboration with the Cancer Genome Anatomy Project (CGAP) (5), the analyses of these libraries was extended from a total of 123,046 transcripts in the previously published work to 195,160 transcripts in the current work. Tags were extracted from the raw sequence data and, after excluding repeated ditags, linker sequences, and tags from the polyrnorphic Major Histocompatibility loci, the resulting tag libraries were compared and statistical analysis performed using SAGE software, version 4.0. Data from the libraries are publicly available at the Uniform Resource Locator (URL) address for the http file type found on the www host server that has a domain name of ncbi.nlm.nih.gov, and a path to the directory SAGE, and detailed SAGE protocols are available at the Uniform Resource Locator (URL) address for the http file type found on the www host server that has a domain name of sagenet.org, and file name of sage_protocol.htn.

Example 2

RT-PCR

Figure 2:
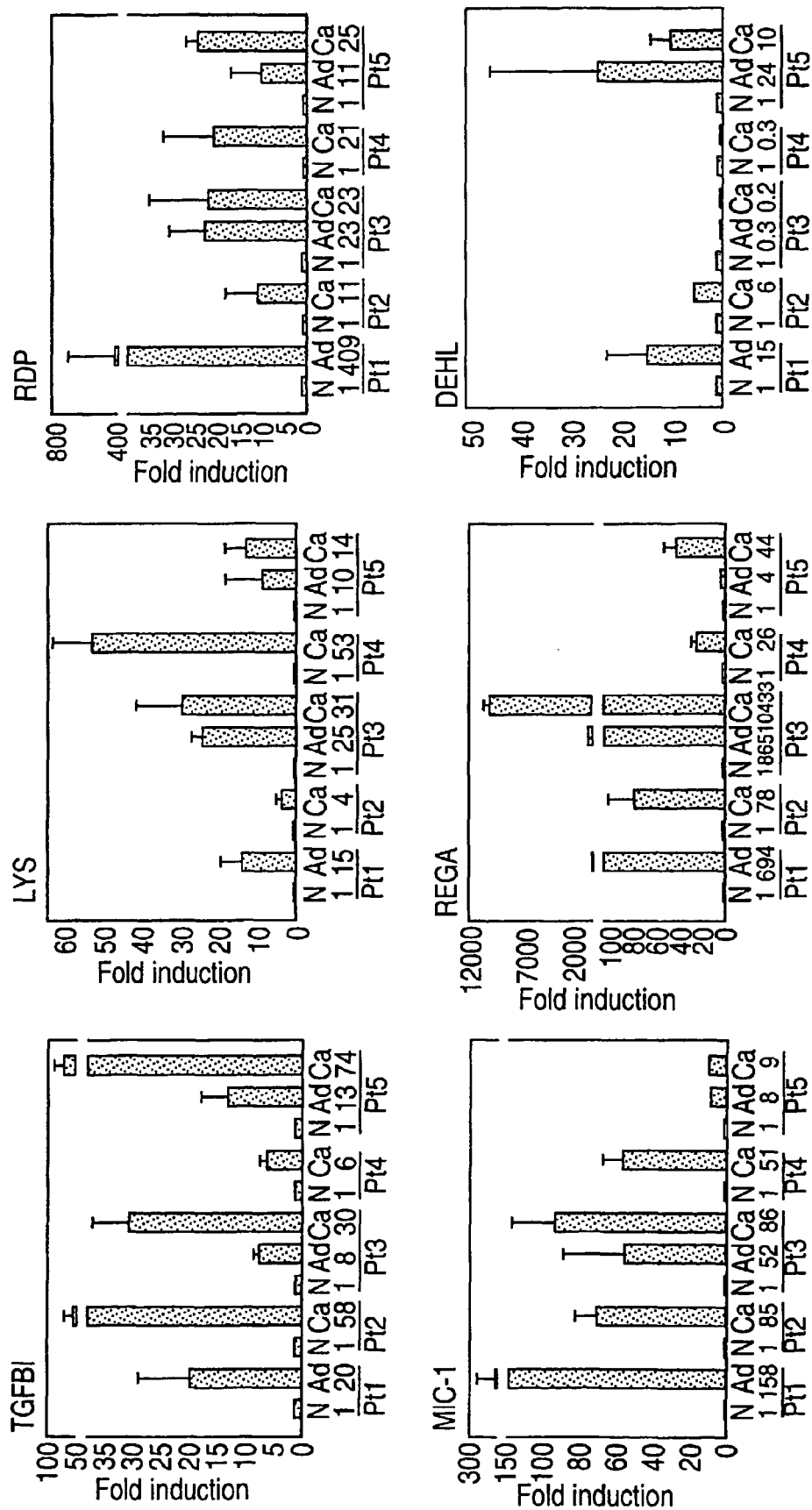
FIG. 2. Quantitative PCR analysis of genes elevated in both adenomas and cancers. Quantitation of expression of genes in tumors and matched normal tissues from five patients (Pt) are shown as fold elevation over that in matched normal colonic mucosa. Each bar represents the average of three independent measurements. TGFBI, LYS, RDP, MIC-1, REGA, and DEHL are as described in Table 3.
Figure 3:
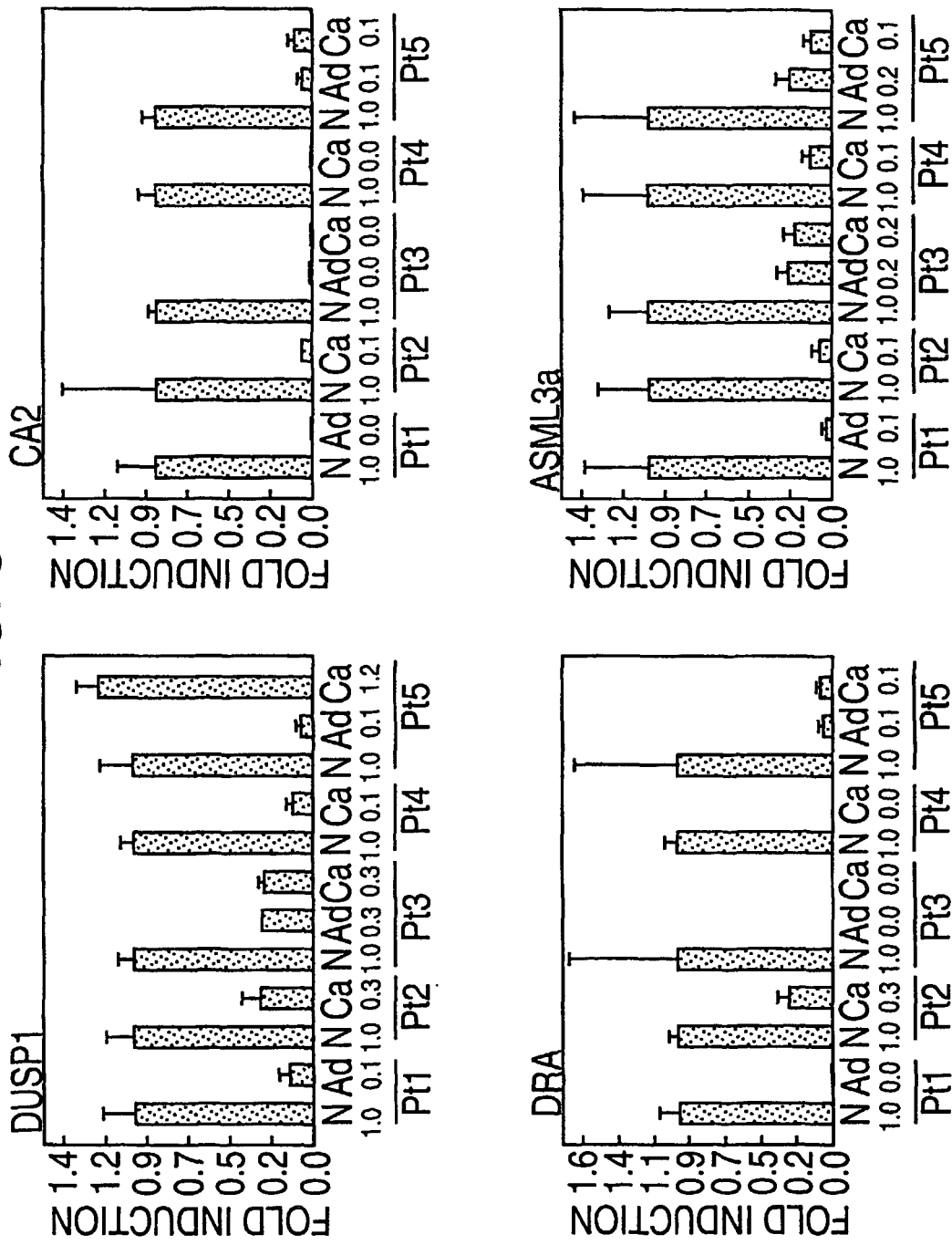
FIG. 3. Quantitative PCR analysis of genes decreased in both adenomas and cancers. Quantitation of expression of genes in tumors and matched normal tissue from five patients (Pt) are shown as a fraction of matched normal. Each bar represents the average of three independent measurements. CA2 and DRA are described in Table 4. Dual Specificity Phosphatase (DUSP1), and Acid Sphingomylenase-like phosphodiesterase (ASML3a) represented transcripts that were repressed but did not meet the stringent criteria required for inclusion in Table 4. SAGE data indicated that DUSP1 was 5- and 76-fold repressed in adenomas and cancers, respectively. ASML3a was 15-fold repressed in both adenoma and cancer.

To verify the increased expression of these six genes, we used quantitative RT-PCR techniques to analyze the expression in seven colorectal neoplasms (three sporadic adenomas and four sporadic cancers) and matched normal colonic mucosa. For these assays, specific primers were developed that resulted in amplification from cDNA but not genomic DNA. Controls were provided by similar quantitative PCR assays of a gene whose expression was found to be very similar in the SAGE libraries of normal and neoplastic colon (β-amyloid precursor protein). The quantitative PCR experiments verified that five of the six selected genes (TGFBI, LYS, RDP, MIC-1, REGA) were expressed at significantly higher levels in every neoplastic sample analyzed compared to patient-matched normal mucosa (FIG. 2). Several tumors exhibited ≧20-fold higher levels of the studied transcripts compared to their patient-matched normal colonic mucosa, as predicted by SAGE. Another control was provided by the quantitative PCR analysis of four genes whose expression was observed to be reduced in the SAGE libraries prepared from adenomas and cancers compared to those from normal colonic mucosa. As shown in FIG. 3, the quantitative PCR confirmed the lower levels of expression of each of these genes, emphasizing that the dramatic elevations in expression observed in FIG. 2 represented gene-specific phenomena. Quantitative PCR. Tumors were collected, snap frozen, and stored at −80° C. They were verified to be predominantly composed of neoplastic cells by histopathological analysis, mRNA was isolated from tumors and patient-matched normal colonic mucosa using QuickPrep reagents (Amersham Pharmacia Biotech UK, Buckinghamshire, England), and single-stranded cDNA was synthesized using Superscript II (Life Technologies, Gaithersburg, Md.). Quantitative PCR was performed using an iCycler (Bio-Rad, Hercules, Calif.), and threshold cycle numbers determined using iCycler software, version 2.1. Reactions were performed in triplicate and threshold cycle numbers averaged. All genes examined were normalized to a control gene (β-amyloid precursor protein, shown by SAGE to be expressed at equivalent levels in all colorectal samples), and fold induction calculated according to the formula $2^{(Rt-Et)}/2^{(Rn-En)}$ where Rt is the threshold cycle number for the Reference gene observed in the tumor, Et is the threshold cycle number for the Experimental gene observed in the tumor, Rn is the threshold cycle number for the Reference gene observed in the normal, and En is the threshold cycle number for the Experimental gene observed in the normal. The primers used for quantitative PCR were obtained from GeneLink (Hawthorne, N.Y.), and their sequences are available upon request.

Example 3

Expression in Isolated Epithelial Cells

Figure 4:
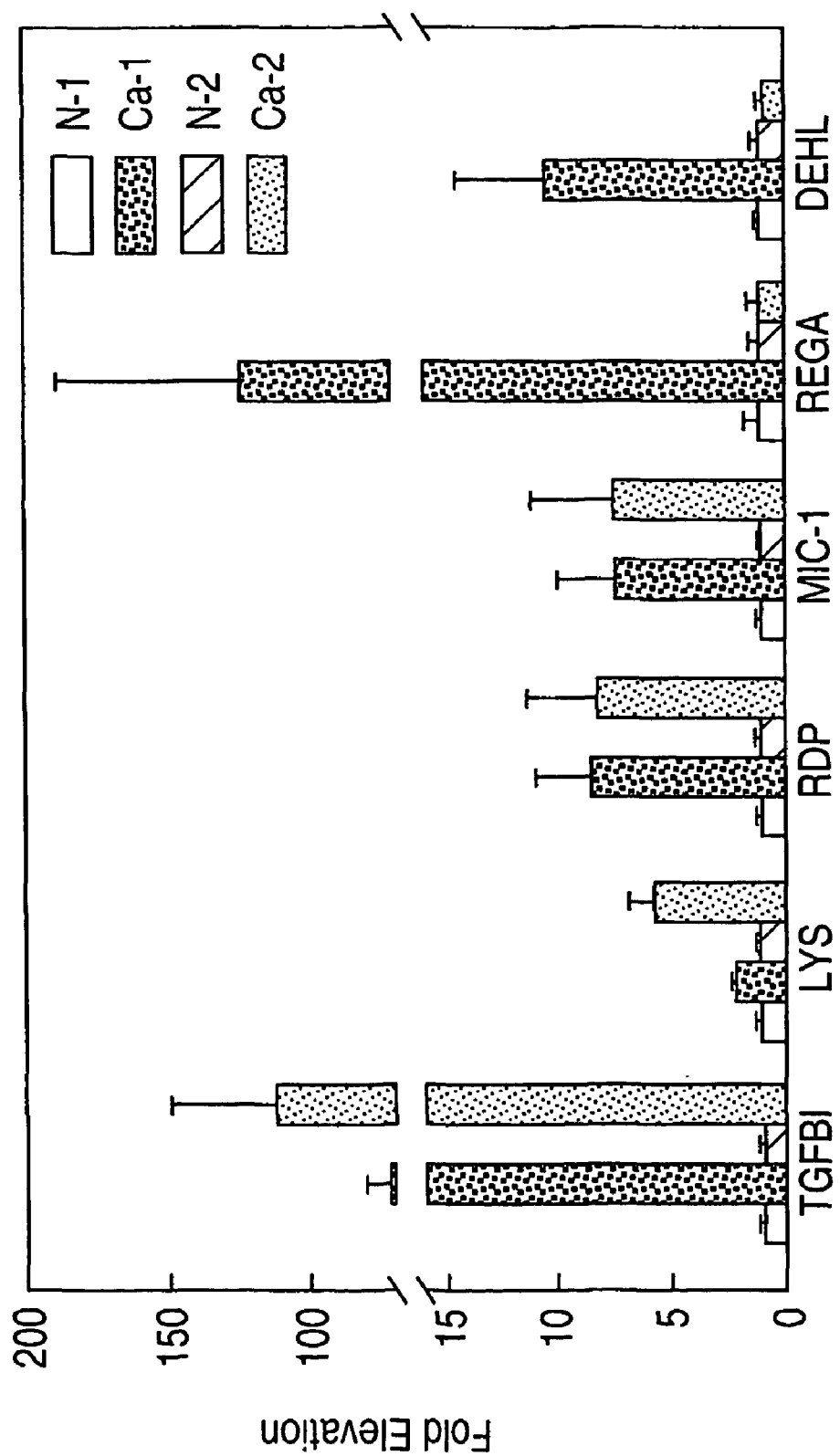
FIG. 4. Quantitative PCR analysis of mRNA from purified epithelial cells of genes elevated in both adenomas and cancers. Quantitation of expression of genes in the purified normal (N) or cancer (Ca) epithelial cells taken from two patients are shown as fold elevation over matched normal. Genes examined were the same as in FIG. 2.

The quantitative PCR data obtained from mRNA isolated from whole tumors provided independent evidence that SAGE provided an accurate indication of gene expression changes in colorectal neoplasia. However, neither analysis identified the cell types responsible for the increased expression. Non-neoplastic stromal cells within tumors may be considerably different than those in normal colonic mucosa (6), and the epithelial derivation of gene expression differences cannot reliably be concluded without direct supporting evidence. We therefore sought to determine if the epithelial cells of cancers express elevated levels of the six genes depicted in FIG. 2. First, we affinity-purified cancerous and patient-matched normal epithelial cells from fresh surgical specimens using immunomagnetic beads directed to the pan epithelial marker Ber-EP4, prepared cDNA and performed quantitative PCR analysis to determine the expression levels of the elevated genes as above. Elevated expression was observed in the purified tumor epithelial cells for each of the six genes examined (FIG. 4), demonstrating that at least some of the increased expression was derived from epithelial cells. However, relative expression of LYS was not as prominent or reproducible in the purified epithelial cells as in the mRNA from the unfractionated tumors, suggesting that other cell types might have contributed transcripts from this gene.

Epithelial cell immunoaffinity purification. Tumor epithelial cells were purified using a modification of the procedure previously developed for the isolation of tumor endothelial cells (6). In brief, fresh surgical specimens of tumor and matched normal tissue were obtained and digested with collagenase and the resulting material filtered through a nylon mesh to obtain single cell suspensions. The cells were then bound to a mixture of anti-CD14 and anti-CD45 immunomagnetic beads (Dynal, Oslo, Norway) to deplete the population of hematopoetic cells (negative selection). The remaining cell suspension was then incubated with anti-Ber-EP4 immunomagnetic beads to isolate epithelial cells (positive selection). Purified cells were lysed directly on the beads and mRNA purified using QuickPrep reagents (Amersham Pharmacia Biotech UK, Buckinghamshire, England).

Example 4

In situ Hybridization in Multiple Tumors

We performed in situ hybridization to RNA in frozen sections of tumors for five of the genes showing the most consistent elevation. DEHL was found to be elevated in only five of the nine tumors examined and was not investigated further. To increase the sensitivity of detection, we generated several RNA probes for each tested gene using in vitro transcription techniques. The results obtained are discussed below in conjunction with brief overviews of each of the five genes of interest.

In situ Hybridization. Non-radioactive in situ hybridization was performed as described (6). For each gene analyzed, a cocktail of anti-sense probes made through in vitro transcription were employed to increase sensitivity. The primers used to generate templates for the synthesis of the in situ riboprobes were obtained from GeneLink (Hawthorne, N.Y.), and their sequences are available upon request.

The results summarized above show that although a large number of tags are observed in the colorectal tissues analyzed, only a small fraction (957/21,343, <5%) were expressed differentially in benign or malignant neoplastic tissues. A similarly small fraction of genes (66/4000, 1.7%) were found to be aberrantly expressed in colorectal neoplasms using oligonucleotide arrays (22). Analysis of these differentially expressed genes not only has the potential to provide insights into the biology of human neoplasia but also may have clinically useful applications. One of the most exciting potential applications concerns the identification of genes whose products provide cellular and serum markers for colorectal neoplasia. In the current study, we identified several genes that appeared to meet all of these criteria and may therefore be especially useful as diagnostic tools for the early detection of presymptomatic colorectal neoplasia. Indeed, the product of one of these genes (MIC-1), has recently been found to be elevated in the serum of patients with colorectal and other cancers, providing further validation of this approach (24).

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

TABLE 5

| Tag_Sequence | NC1 | NC2 | AD1 | AD2 | CA1 | CA2 | UNI ID | Description |
| --- | --- | --- | --- | --- | --- | --- | --- | --- |
| AAAAGAAACT | 1 | 3 | 33 | 52 | 7 | 16 | 172182 | poly(A)-binding protein, cytoplasmic 1 |
| AACGAGGAAT | 8 | 0 | 24 | 26 | 17 | 23 | | |
| AAGAAGATAG | 6 | 6 | 28 | 25 | 21 | 34 | 184776 | ribosomal protein L23a |
| AATAGGTCCA | 12 | 9 | 32 | 36 | 22 | 22 | 113029 | ribosomal protein S25 |
| ACAACTCAAT | 1 | 1 | 7 | 7 | 8 | 6 | 244125 | EST |
| ACAACTCAAT | 1 | 1 | 7 | 7 | 8 | 6 | 75922 | brain protein 13 |
| ACATCATCGA | 10 | 18 | 50 | 66 | 34 | 46 | 182979 | ribosomal protein L12 |
| ACCATTGGAT | 0 | 0 | 3 | 10 | 3 | 9 | 146360 | interferon induced transmembrane protein 1 (9-27) |
| ACCTGTATCC | 5 | 3 | 20 | 6 | 26 | 35 | 182241 | interferon induced transmembrane protein 3 (1-80) |
| ACTCCAAAAA | 9 | 12 | 21 | 65 | 21 | 37 | 133230 | ribosomal protein S15 |
| AGCACCTCCA | 37 | 37 | 108 | 81 | 57 | 108 | 75309 | eukaryotic translation elongation factor 2 |
| AGGACCATCG | 0 | 0 | 8 | 2 | 1 | 18 | | |
| AGGGCTTCCA | 26 | 41 | 74 | 108 | 50 | 85 | 29797 | ribosomal protein L10 |
| ATGGCTGGTA | 18 | 46 | 79 | 75 | 81 | 136 | 182426 | ribosomal protein S2 |
| ATGTAAAAAA | 0 | 0 | 26 | 32 | 2 | 12 | 178112 | DNA segment, single copy probe LNS-CAI/LNS-CAII (deleted in polyposis |
| ATGTAAAAAA | 0 | 0 | 26 | 32 | 2 | 12 | 234734 | lysozyme (renal amyloidosis) |
| ATGTAAAAAA | 0 | 0 | 26 | 32 | 2 | 12 | 83715 | Sjogren syndrome antigen B (autoantigen La) |
| ATTCTCCAGT | 8 | 20 | 20 | 48 | 43 | 28 | 234518 | ribosomal protein L23 |
| CAAGGACCAG | 0 | 0 | 5 | 6 | 10 | 12 | 109 | dipeptidase 1 (renal) |
| CAATAAATGT | 8 | 6 | 40 | 76 | 33 | 67 | 179779 | ribosomal protein L37 |
| CAGCTCACTG | 4 | 17 | 9 | 35 | 21 | 24 | 158675 | ribosomal protein L14 |
| CATTTGTAAT | 48 | 27 | 102 | 57 | 36 | 125 | | |
| CCTAGCTGGA | 16 | 27 | 58 | 45 | 48 | 66 | 182937 | peptidylprolyl isomerase A (cyclophilin A) |
| CCTTCGAGAT | 6 | 12 | 13 | 29 | 7 | 41 | 76194 | ribosomal protein S5 |
| CTCCTCACCT | 7 | 13 | 38 | 36 | 24 | 75 | 242908 | lecithin-cholesterol acyltransferase |
| CTGACTTGTG | 0 | 0 | 1 | 20 | 9 | 2 | 77961 | major histocompatibility complex, class I, B |
| CTGGGTTAAT | 14 | 24 | 84 | 83 | 42 | 112 | 126701 | ribosomal protein S19 |
| CTGTTGATTG | 13 | 3 | 60 | 38 | 32 | 27 | 249495 | heterogeneous nuclear ribonucleoprotein A1 |
| CTGTTGGTGA | 9 | 19 | 37 | 59 | 31 | 61 | 3463 | ribosomal protein S23 |
| GAAAAATGGT | 7 | 12 | 49 | 47 | 25 | 27 | 181357 | laminin receptor 1 (67 kD, ribosomal protein SA) |
| GAGTCAGGAG | 2 | 0 | 8 | 6 | 9 | 7 | 181271 | CGI-120 protein |
| GCATAATAGG | 11 | 16 | 22 | 54 | 50 | 21 | 184108 | ribosomal protein L21 (gene or pseudogene) |
| GCATTTAAAT | 1 | 2 | 10 | 18 | 12 | 7 | 261802 | eukaryotic translation elongation factor 1 beta 1 |
| GCATTTAAAT | 1 | 2 | 10 | 18 | 12 | 7 | 275959 | eukaryotic translation elongation factor 1 beta 2 |
| GCATTTGACA | 2 | 5 | 27 | 17 | 9 | 20 | 172129 | *Homo sapiens* cDNA: FLJ21409 fis, clone COL03924 |
| GCTTTTAAGG | 2 | 8 | 14 | 32 | 16 | 17 | 8102 | ribosomal protein S20 |
| GGACCACTGA | 18 | 39 | 76 | 57 | 48 | 83 | 119598 | ribosomal protein L3 |
| GGGGGTAACT | 1 | 2 | 8 | 11 | 14 | 13 | 99969 | fusion, derived from t(12;16) malignant liposarcoma |
| GTGCGCTGAG | 0 | 0 | 75 | 0 | 20 | 18 | 277477 | major histocompatibility complex, class I, C |
| GTGCTCATTC | 0 | 0 | 13 | 7 | 2 | 10 | 116577 | prostate differentiation factor |
| GTGCTCATTC | 0 | 0 | 13 | 7 | 2 | 10 | 25945 | ESTs |
| GTGTGTTTGT | 0 | 0 | 17 | 29 | 17 | 15 | 118787 | transforming growth factor, beta-induced, 68 kD |
| GTTCGTGCCA | 1 | 13 | 18 | 43 | 24 | 18 | 179606 | nuclear RNA helicase, DECD variant of DEAD box family |
| GTTCGTGCCA | 1 | 13 | 18 | 43 | 24 | 18 | 179666 | uncharacterized hypothalamus protein HSMNP1 |
| TAATAAAGGT | 4 | 11 | 37 | 62 | 24 | 27 | 151604 | ribosomal protein S8 |
| TAATTTTTGC | 0 | 1 | 99 | 12 | 20 | 37 | 273321 | differentially expressed in hematopoietic lineages |
| TCACAAGCAA | 10 | 7 | 17 | 21 | 13 | 38 | 146763 | nascent-polypeptide-associated complex alpha polypeptide |

TABLE 5-continued

| Tag_Sequence | NC1 | NC2 | AD1 | AD2 | CA1 | CA2 | UNI ID | Description |
|---|---|---|---|---|---|---|---|---|
| TCAGATCTTT | 14 | 32 | 37 | 108 | 31 | 87 | 75344 | ribosomal protein S4, X-linked |
| TCCTGCCCCA | 1 | 5 | 10 | 14 | 7 | 16 | 171814 | parathymosin |
| TGAAATAAAA | 0 | 2 | 2 | 14 | 13 | 11 | 173205 | nucleophosmin (nucleolar phosphoprotein B23, numatrin) |
| TGAAATAAAA | 0 | 2 | 2 | 14 | 13 | 11 | 192822 | Human DNA sequence from clone RP5-1179L24 on chromosome 6q24.3-25.3. Contains the 3' end of the gene for a novel protein similar to mouse phospholipase C neighboring protein PNG, ESTs, STSs and GSSs |
| TGATGTCTGG | 0 | 0 | 2 | 6 | 8 | 2 | 83883 | transmembrane, prostate androgen induced RNA |
| TGTAATCAAT | 2 | 3 | 13 | 11 | 8 | 11 | 249495 | heterogeneous nuclear ribonucleoprotein A1 |
| TTACCATATC | 10 | 5 | 22 | 30 | 26 | 22 | 300141 | ribosomal protein L39. |
| TTATGGGATC | 6 | 4 | 24 | 37 | 36 | 47 | 5662 | guanine nucleotide binding protein (G protein), beta polypeptide 2-like 1 |
| TTCAATAAAA | 8 | 14 | 79 | 111 | 36 | 50 | 177592 | ribosomal protein, large, P1 |
| TTCCAGCTGC | 0 | 0 | 7 | 6 | 2 | 9 | 112442 | ESTs, Weakly similar to |
| TTCCAGCTGC | 0 | 0 | 7 | 6 | 2 | 9 | 19121 | adaptor-related protein complex 2, alpha 2 subunit |
| TTCCAGCTGC | 0 | 0 | 7 | 6 | 2 | 9 | 227277 | sine oculis homeobox (*Drosophila*) homolog 3 |
| TTTCCACTAA | 0 | 0 | 8 | 4 | 4 | 6 | 1032 | regenerating isler-derived 1 alpha (pancreatic stone protein, pancreatic thread protein) |
| TTTCCACTAA | 0 | 0 | 8 | 4 | 4 | 6 | 289088 | heat shock 90 kD protein 1, alpha |
| TTTTTAATGT | 0 | 2 | 12 | 18 | 6 | 7 | 161307 | H3 histone, family SA |

TABLE 6

| Tag_Sequence | NC1 | NC2 | AD1 | AD2 | CA1 | CA2 | UNI ID | Description |
|---|---|---|---|---|---|---|---|---|
| AAATCTGGCA | 16 | 15 | 2 | 4 | 2 | 0 | 430 | plastin 1 (I isoform) |
| AACGTGCAGG | 29 | 31 | 13 | 6 | 7 | 8 | 160786 | argininosuccinate synthetase |
| AAGAAAGCTC | 20 | 6 | 0 | 2 | 1 | 5 | 25264 | DKFZP434N126 protein |
| AAGAAAGCTC | 20 | 6 | 0 | 2 | 1 | 5 | 91011 | anterior gradient 2 (*Xenopus laevis*) homolog |
| AAGAAGCAGG | 8 | 16 | 3 | 4 | 1 | 3 | 11441 | chromosome 1 open reading frame 8 |
| AAGGTAGCAG | 15 | 16 | 2 | 4 | 2 | 4 | 104125 | adenylyl cyclase-associated protein |
| AATAAAGGCT | 25 | 11 | 3 | 7 | 3 | 4 | 179735 | ras homolog gene family, member C |
| AATAGTTTCC | 7 | 16 | 2 | 3 | 6 | 1 | 272620 | pregnancy specific beta-1-glycoprotein 9 |
| AATCACAAAT | 18 | 45 | 1 | 4 | 14 | 3 | 74466 | carcinoembryonic antigen-related cell adhesion molecule 7 |
| AATGAGAAGG | 11 | 3 | 0 | 0 | 1 | 0 | 198248 | UDP-Gal:betaGlcNAc beta 1,4-galactosyltransferase, polypeptide 1 |
| ACAATTGGTC | 0 | 10 | 0 | 0 | 0 | 0 | 155097 | carbonic anhydrase II |
| ACACCCATCA | 2 | 27 | 1 | 0 | 5 | 3 | 110445 | CGI-97 protein |
| ACAGGGTGAC | 25 | 13 | 1 | 8 | 7 | 6 | 174050 | endothelial differentiation-related factor 1 |
| ACATTGGGTG | 377 | 334 | 67 | 34 | 96 | 33 | 275086 | PR domain containing 10 |
| ACATTGGGTG | 377 | 334 | 67 | 34 | 96 | 33 | 5241 | fatty acid binding protein 1, liver |
| ACCCAACTGC | 12 | 3 | 0 | 0 | 0 | 0 | 232604 | Homo sapiens cDNA: FLJ22675 fis, clone HSI10553 |
| ACCCACGTCA | 22 | 10 | 3 | 5 | 3 | 1 | 198951 | jun B proto-oncogene |
| ACCCCCCCGC | 44 | 38 | 7 | 13 | 16 | 6 | 229413 | ESTs |
| ACCCCCCCGC | 44 | 38 | 7 | 13 | 16 | 6 | 2780 | jun D proto-oncogene |
| ACCTGCATCC | 0 | 12 | 0 | 0 | 0 | 0 | | |
| ACCTGGGGAG | 35 | 11 | 1 | 3 | 4 | 3 | 131748 | ESTs, Moderately similar to |
| ACCTGGGGAG | 35 | 11 | 1 | 3 | 4 | 3 | 209119 | 1-acylglycerol-3-phosphate O-acyltransferase 2 (lysophosphatidic acid acyltransferase, beta) |
| ACGGTCCAGG | 5 | 12 | 0 | 0 | 0 | 1 | 72924 | cytidine deaminase |
| ACTCTTGTTG | 7 | 2 | 0 | 0 | 0 | 0 | 5378 | spondin 1, (f-spondin) extracellular matrix protein |
| ACTGTGGCGG | 17 | 34 | 9 | 12 | 9 | 4 | 112242 | ESTs |
| AGAATAGCTT | 44 | 67 | 3 | 9 | 11 | 30 | 24133 | ESTs |
| AGCAGGAGCA | 50 | 14 | 6 | 3 | 7 | 6 | 178292 | KIAA0180 protein |
| AGCAGGAGCA | 50 | 14 | 6 | 3 | 7 | 6 | 738 | early growth response 1 |
| AGCCCGACCA | 16 | 8 | 2 | 4 | 1 | 3 | 104114 | H. sapiens HCG I mRNA |
| AGGATGGTCC | 34 | 19 | 5 | 3 | 6 | 8 | 71779 | Homo sapiens DNA from chromosome 19, cosmld F21856 |
| AGGCCAAGGG | 21 | 6 | 3 | 1 | 3 | 4 | 76057 | galactose-4-epimerase, UDP |
| AGGTGACTGG | 10 | 14 | 0 | 0 | 0 | 0 | | |
| AGTGGGCTCA | 3 | 8 | 0 | 1 | 0 | 0 | | |
| ATACTCCACT | 82 | 59 | 0 | 0 | 10 | 3 | 778 | guanylate cyclase activator 1B (retina) |
| ATATAATCTG | 18 | 14 | 1 | 4 | 5 | 5 | 621 | lectin, galactoside-binding, soluble, 3 (galectin 3) |
| ATCGTGGCGG | 193 | 92 | 19 | 25 | 20 | 10 | 5372 | claudin 4 |
| ATGACGCTCA | 22 | 18 | 6 | 5 | 3 | 4 | 8254 | hypothetical protein PRO0899 |
| ATGATGGCAC | 12 | 32 | 0 | 0 | 1 | 0 | 84072 | transmembrane 4 superfamily member 3 |
| ATGCGGAGTC | 14 | 13 | 5 | 3 | 2 | 4 | 25527 | tight junction protein 3 (zona occludens 3) |
| ATGCGGGAGA | 38 | 39 | 15 | 22 | 5 | 6 | 109748 | Homo sapiens CAC-1 mRNA, partial cds |
| ATGGCACGGA | 6 | 21 | 1 | 1 | 3 | 0 | 81097 | cytochrome C oxidase subunit VIII |
| ATGGTCTACG | 10 | 5 | 0 | 0 | 0 | 0 | 96593 | hypothetical protein |
| ATGGTGGGGG | 25 | 30 | 11 | 9 | 1 | 2 | 1665 | zinc finger protein homologous to Zfp-36 in mouse |
| ATGTGCGTGG | 38 | 8 | 11 | 3 | 7 | 7 | 56937 | suppression of tumorigenicity 14 (colon carcinoma, matriptase, epithin) |
| ATGTGGGCTC | 7 | 2 | 0 | 0 | 0 | 0 | 151641 | glycoprotein A repetitions predominant |
| ATGTGGGCTC | 7 | 2 | 0 | 0 | 0 | 0 | 27018 | Ris |
| ATTGGAGTGC | 136 | 85 | 15 | 36 | 37 | 19 | 220529 | carcinoembryonic antigen-related cell adhesion molecule 5 |
| ATTTCAAGAT | 35 | 21 | 0 | 2 | 1 | 0 | 155097 | carbonic anhydrase II |
| ATTTCAAGAT | 35 | 21 | 0 | 2 | 1 | 0 | 24453 | ESTs |
| CAAATAAAAG | 9 | 12 | 2 | 0 | 1 | 1 | 185055 | BENE protein |
| CAAGAGTTTC | 14 | 2 | 0 | 0 | 0 | 0 | 183617 | ESTs |

TABLE 6-continued

| Tag_Sequence | NC1 | NC2 | AD1 | AD2 | CA1 | CA2 | UNI ID | Description |
|---|---|---|---|---|---|---|---|---|
| CACCCCTGAT | 73 | 169 | 58 | 58 | 13 | 36 | 173724 | creatine kinase, brain |
| CAGTGCGTTC | 12 | 3 | 0 | 0 | 3 | 0 | 8302 | four and a half LIM domains 2 |
| CATAGGTTTA | 66 | 39 | 4 | 1 | 5 | 0 | 1650 | solute carrier family 26, member 3 |
| CCAAAGCTAT | 42 | 16 | 14 | 12 | 6 | 11 | 84072 | transmembrane 4 superfamily member 3 |
| CCAACACCAG | 9 | 19 | 1 | 0 | 0 | 1 | 181165 | eukaryotic translation elongation factor 1 alpha 1 |
| CCACTGCACC | 21 | 19 | 5 | 5 | 6 | 14 | | |
| CCAGGGGAGA | 45 | 66 | 24 | 22 | 10 | 20 | 278613 | interferon, alpha-inducible protein 27 |
| CCATTCCACT | 13 | 1 | 2 | 0 | 0 | 0 | | |
| CCCAACGCGC | 106 | 1 | 3 | 5 | 0 | 2 | 272572 | hemoglobin, alpha 2 |
| CCCCGAAGC | 25 | 27 | 3 | 15 | 4 | 8 | 61265 | ESTs, Weakly similar to |
| CCCCCGCGGA | 33 | 25 | 6 | 11 | 4 | 12 | 95697 | liver-specific bHLH-Zip transcription factor |
| CCCCCTGCAT | 5 | 4 | 0 | 0 | 0 | 0 | | |
| CCCGCCTCTT | 0 | 40 | 3 | 3 | 16 | 1 | mito | Tag matches mitochondrial sequence |
| CCCTCCCGAA | 89 | 54 | 9 | 14 | 18 | 7 | 5940 | hypothetical protein FLJ20063 |
| CCGCTGCACT | 127 | 102 | 55 | 46 | 37 | 30 | | |
| CCGGCTTGAG | 7 | 4 | 0 | 0 | 0 | 0 | 2722 | inositol 1,4,5-trisphosphate 3-kinase A |
| CCTCCAGCTA | 715 | 458 | 142 | 125 | 131 | 147 | 242463 | keratin 8 |
| CCTCCAGTAC | 20 | 8 | 2 | 3 | 2 | 4 | | |
| CCTGCCCCCC | 20 | 30 | 6 | 3 | 11 | 4 | 861 | mitogen-activated protein kinase 3 |
| CCTGCTGCAG | 7 | 34 | 0 | 1 | 6 | 9 | 102482 | mucin 5, subtype B, tracheobronchial |
| CCTGCTTGTC | 20 | 23 | 0 | 3 | 0 | 5 | 268171 | ESTs, Weakly similar to |
| CCTGCTTGTC | 20 | 23 | 0 | 3 | 0 | 5 | 2719 | epididymis-specific, whey-acidic protein type, four-disulfide core; putative ovarian carcinoma marker |
| CCTGGAAGAG | 30 | 26 | 11 | 4 | 12 | 16 | 75655 | procollagen-proline, 2-oxoglutarate 4-dioxygenase (proline 4-hydroxylase), beta polypeptide (protein disulfide isomerase; thyroid hormone binding protein p55) |
| CCTGTCTGCC | 14 | 22 | 0 | 1 | 1 | 1 | 107139 | hypothetical protein |
| CCTGTGACAG | 22 | 27 | 0 | 4 | 3 | 1 | 120 | anti-oxidant protein 2 (non-selenium glutathione peroxidase, acidic calcium-independent phospholipase A2) |
| CCTTCAAATC | 29 | 17 | 0 | 0 | 1 | 0 | 23118 | carbonic anhydrase I |
| CGAGGGGCCA | 110 | 47 | 18 | 18 | 12 | 32 | 182485 | actinin, alpha 4 |
| CGCTGTGGGG | 58 | 53 | 19 | 8 | 8 | 6 | 7486 | protein expressed in thyroid |
| CGGACTCACT | 20 | 45 | 5 | 14 | 14 | 10 | 284134 | serologically defined colon cancer antigen 28 |
| CGGACTCACT | 20 | 45 | 5 | 14 | 14 | 10 | 84700 | similar to phosphatidylcholine transfer protein 2 |
| CGGGAGTCGG | 28 | 30 | 13 | 2 | 9 | 1 | 236720 | ESTs, Weakly similar to |
| CGGTGGGACC | 7 | 14 | 1 | 1 | 3 | 3 | 99175 | Homo sapiens cDNA: FLJ21606 fis, clone COL07302 |
| CGTGGGTGGG | 1 | 10 | 1 | 0 | 0 | 1 | 202833 | heme oxygenase (decycling) 1 |
| CTAGCCTCAC | 172 | 90 | 30 | 53 | 36 | 58 | 14376 | actin, gamma 1 |
| CTCAGAACTT | 18 | 3 | 1 | 0 | 0 | 0 | 194710 | glucosaminyl (N-acetyl) transferase 3, mucin type |
| CTGAACCTCG | 5 | 15 | 2 | 0 | 0 | 0 | 4205 | hypothetical protein FLJ20124 |
| CTGACCTGTG | 88 | 130 | 48 | 18 | 16 | 46 | 77961 | major histocompatibility complex, class I, B |
| CTGGATCTGG | 21 | 21 | 3 | 9 | 5 | 10 | 75658 | phosphorylase, glycogen; brain |
| CTGGCAAAGG | 14 | 22 | 1 | 0 | 0 | 0 | | |
| CTGGCCCTCG | 186 | 52 | 1 | 3 | 15 | 14 | 1406 | trefoil factor 1 (breast cancer, estrogen-inducible sequence expressed in) |
| CTGGCCCTCG | 186 | 52 | 1 | 3 | 15 | 14 | 166184 | Intersectin 2 |
| CTGGCCCTCG | 186 | 52 | 1 | 3 | 15 | 14 | 7720 | dynein, cytoplasmic, heavy polypeptide 1 |
| CTGGCTATCC | 7 | 3 | 0 | 0 | 0 | 1 | 10784 | hypothetical protein FLJ20037 |
| CTGGGCCTCG | 22 | 22 | 2 | 2 | 3 | 3 | 50868 | solute carrier family 22 (organic cation transporter), member 1-like |
| CTGTACTTGT | 9 | 5 | 1 | 1 | 0 | 0 | 75678 | FBJ murine osteosarcoma viral oncogene homolog B |
| CTGTGTGGCT | 0 | 12 | 1 | 0 | 0 | 0 | 127610 | acyl-Coenzyme A dehydrogenase, C-2 to C-3 short chain |
| CTGTGTGGCT | 0 | 12 | 1 | 0 | 0 | 0 | 54277 | DNA segment on chromosome X (unique) 9928 expressed sequence |
| CTTACAAGCA | 21 | 13 | 2 | 3 | 4 | 3 | mito | Tag matches mitochondrial sequence |
| CTTAGAGGGG | 16 | 22 | 0 | 1 | 1 | 1 | 155191 | villin 2 (ezrin) |
| CTTATGGTCC | 36 | 11 | 0 | 1 | 1 | 0 | 179608 | retinol dehydrogenase homolog |
| CTTCCAGCTA | 64 | 31 | 22 | 20 | 14 | 19 | 217493 | annexin A2 |
| CTTCTTGCCC | 29 | 2 | 2 | 2 | 0 | 1 | 251577 | hemoglobin, alpha 1 |
| CTTGACATAC | 18 | 20 | 4 | 4 | 0 | 0 | 171695 | dual specificity phosphatase 1 |
| CTTGATTCCC | 26 | 9 | 5 | 0 | 2 | 5 | 77266 | quiescin Q6 |
| GACATCAAGT | 198 | 87 | 23 | 14 | 47 | 17 | 182265 | keratin 19 |
| GACCAGCCCA | 23 | 21 | 3 | 2 | 12 | 5 | 75799 | protease, serine, 8 (prostasin) |
| GACCAGTCGA | 21 | 44 | 4 | 0 | 2 | 0 | 143131 | glycoprotein A33 (transmembrane) |
| GACGCGGCGC | 30 | 47 | 10 | 17 | 12 | 17 | 301684 | RNA POLYMERASE I AND TRANSCRIPT RELEASE FACTOR |
| GAGAGCTCCC | 5 | 11 | 3 | 0 | 2 | 1 | mito | Tag matches mitochondrial sequence |
| GAGCACCGTG | 7 | 4 | 1 | 0 | 0 | 1 | | |
| GATATGTAAA | 1 | 10 | 0 | 0 | 0 | 0 | | |
| GATCCCAACT | 9 | 29 | 5 | 7 | 1 | 1 | 118786 | metallothionein 2A |
| GATGAATCCG | 12 | 14 | 2 | 2 | 1 | 2 | 283552 | ESTs, Weakly similar to |
| GATGACCCCC | 42 | 49 | 4 | 3 | 3 | 3 | mito | Tag matches mitochondrial sequence |
| GCAAGAAAGT | 48 | 0 | 0 | 4 | 0 | 1 | 155376 | hemoglobin, beta |
| GCACAGGTCA | 5 | 9 | 1 | 0 | 1 | 0 | | |
| GCACCCTTTC | 13 | 5 | 0 | 0 | 1 | 0 | | |
| GCACCTGTCG | 2 | 9 | 0 | 0 | 1 | 0 | 109059 | mitochondrial ribosomal protein L12 |
| GCACCTGTCG | 2 | 9 | 0 | 0 | 1 | 0 | 1239 | alanyl (membrane) aminopeptidase (aminopeptidase N, aminopeptidase M, microsomal aminopeptidase, CD13, p150) |
| GCAGCTCCTG | 13 | 47 | 3 | 2 | 7 | 3 | 119257 | ems1 sequence (mammary tumor and squamous cell carcinoma-associated (p80/85 src substrate) |
| GCAGGAGGTG | 2 | 13 | 0 | 0 | 0 | 1 | 11441 | chromosome 1 open reading frame 8 |
| GCAGGAGGTG | 2 | 13 | 0 | 0 | 0 | 1 | 78040 | KDEL (Lys-Asp-Glu-Leu) endoplasmic reticulum protein retention receptor 1 |

TABLE 6-continued

| Tag_Sequence | NC1 | NC2 | AD1 | AD2 | CA1 | CA2 | UNI ID | Description |
|---|---|---|---|---|---|---|---|---|
| GCAGGGCCTC | 128 | 165 | 41 | 69 | 39 | 51 | 92323 | FXYD domain-containing Ion transport regulator 3 |
| GCCACATACT | 3 | 9 | 0 | 0 | 0 | 0 | 4984 | KIAA0828 protein |
| GCCACGTGGA | 19 | 16 | 5 | 2 | 7 | 1 | 103665 | villin-like |
| GCCAGACACC | 19 | 9 | 3 | 4 | 1 | 2 | 3804 | DKFZP564C1940 protein |
| GCCAGGTTGC | 14 | 5 | 1 | 1 | 1 | 1 | 42824 | hypothetical protein FLJ10718 |
| GCCAGGTTGC | 14 | 5 | 1 | 1 | 1 | 1 | 55682 | eukaryotic translation initiation factor 3, subunit 7 (zeta, 66/67 kD) |
| GCCAGGTTGC | 14 | 5 | 1 | 1 | 1 | 1 | 78996 | proliferating cell nuclear antigen |
| GCCATCCTCC | 9 | 13 | 0 | 1 | 0 | 0 | | |
| GCCCACACAG | 15 | 0 | 1 | 1 | 0 | 0 | 1690 | heparin-binding growth factor binding protein |
| GCCCACGTCA | 7 | 8 | 0 | 0 | 0 | 0 | | |
| GCCCAGGGCC | 4 | 44 | 2 | 1 | 2 | 1 | 10326 | coatomer protein complex, subunit epsilon |
| GCCCAGGGCC | 4 | 44 | 2 | 1 | 2 | 1 | 229417 | EST, Moderately similar to |
| GCCCAGGGCC | 4 | 44 | 2 | 1 | 2 | 1 | 229546 | EST |
| GCCCAGGTCA | 519 | 447 | 136 | 128 | 58 | 22 | 154903 | ESTs, Weakly similar to |
| GCCCAGTGGC | 51 | 0 | 8 | 15 | 2 | 5 | 143131 | glycoprotein A33 (transmembrane) |
| GCCGACCAGG | 46 | 47 | 15 | 8 | 19 | 9 | 75741 | amiloride binding protein 1 (amine oxidase (copper-containing)) |
| GCCGGGTGGG | 207 | 149 | 18 | 24 | 68 | 67 | 74631 | basigin |
| GCCGTGGAGA | 32 | 23 | 4 | 11 | 7 | 7 | 80680 | major vault protein |
| GCCTGGCCAT | 26 | 34 | 4 | 6 | 10 | 14 | 5662 | guanine nucleotide binding protein (G protein), beta polypeptide 2-like 1 |
| GCCTGGCCAT | 26 | 34 | 4 | 6 | 10 | 14 | 63042 | DKFZp564J157 protein |
| GCGAAACCCT | 167 | 565 | 123 | 43 | 64 | 98 | | |
| GCGAAACTCG | 5 | 9 | 1 | 0 | 0 | 0 | | |
| GCGCAGAGGT | 2 | 16 | 1 | 0 | 0 | 1 | 108124 | ribosomal protein L41 |
| GCTCTTCCCC | 9 | 21 | 1 | 2 | 2 | 0 | 33455 | peptidyl arginine deiminase, type II |
| GCTGCCCTTG | 44 | 6 | 13 | 6 | 6 | 18 | 272897 | Tubulin, alpha, brain-specific |
| GCTGCCCTTG | 44 | 6 | 13 | 6 | 6 | 18 | 278242 | tubulin, alpha, ubiquitous |
| GCTGGCACAT | 15 | 14 | 1 | 0 | 6 | 0 | 179704 | meprin A, alpha (PABA peptide hydrolase) |
| GCTGGCCCCG | 5 | 11 | 0 | 0 | 0 | 1 | 8185 | CGI-44 protein; sulfide dehydrogenase like (yeast) |
| GCTGTGCCTG | 36 | 42 | 2 | 4 | 11 | 8 | 58247 | protease, serine, 4 (trypsin 4, brain) |
| GCTTGGGGAT | 11 | 8 | 2 | 0 | 0 | 0 | 5394 | myosin, heavy polypeptide-like (110 kD) |
| GGAACAGGGG | 1 | 13 | 1 | 0 | 0 | 2 | 102336 | Rho GTPase activating protein 8 |
| GGAACAGGGG | 1 | 13 | 1 | 0 | 0 | 2 | 272972 | hypothetical protein FLJ20185 |
| GGAACAGGGG | 1 | 13 | 1 | 0 | 0 | 2 | 77961 | major histocompatibility complex, class I, B |
| GGAACTGTGA | 90 | 84 | 10 | 18 | 10 | 2 | 38972 | tetraspan 1 |
| GGAAGAGCAC | 21 | 11 | 1 | 1 | 2 | 5 | 75268 | sialyltransferase 4C (beta-galactosidase alpha-2,3-sialytransferase) |
| GGAGGCCGAG | 13 | 9 | 5 | 0 | 2 | 5 | 301342 | ESTs, Weakly similar to |
| GGAGGCGCTC | 5 | 11 | 1 | 1 | 0 | 1 | 33455 | peptidyl arginine deiminase, type II |
| GGATGGCTTA | 25 | 5 | 2 | 1 | 1 | 1 | 64179 | hypothetical protein |
| GGCACCGTGC | 22 | 44 | 8 | 10 | 8 | 4 | 120912 | ESTs |
| GGCCCTGCAG | 14 | 7 | 1 | 0 | 5 | 1 | 105463 | sir2-related protein type 6 |
| GGCTCGGGAT | 15 | 11 | 2 | 4 | 3 | 5 | 2575 | calpain 1, (mu/l) large subunit |
| GGCTGCCTGC | 13 | 11 | 4 | 3 | 5 | 2 | 180958 | ESTs |
| GGCTGCCTGC | 13 | 11 | 4 | 3 | 5 | 2 | 197314 | ESTs |
| GGCTGGGCCT | 46 | 25 | 14 | 5 | 10 | 8 | 144102 | EST |
| GGCTGGGCCT | 46 | 25 | 14 | 5 | 10 | 8 | 14846 | Homo sapiens mRNA; cDNA DKFZp564D016 (from clone DKFZp564D016) |
| GGCTGGGCCT | 46 | 25 | 14 | 5 | 10 | 8 | 73919 | clathrin, light polypeptide (Lcb) |
| GGGAAGCAGA | 32 | 17 | 18 | 4 | 8 | 9 | | |
| GGGACGAGTG | 20 | 6 | 1 | 3 | 6 | 1 | 3337 | transmembrane 4 superfamily member 1 |
| GGGCGCTGTG | 11 | 27 | 3 | 6 | 4 | 5 | 8372 | ubiquinol-cytochrome c reductase (6.4 kD) subunit |
| GGGGCAGGGC | 48 | 64 | 27 | 10 | 15 | 31 | 119140 | eukaryotic translation initiation factor 5A |
| GGTGAAGAGG | 16 | 32 | 5 | 3 | 10 | 9 | 233950 | serine protease inhibitor, Kunitz type 1 |
| GTAGCAGGTG | 24 | 27 | 11 | 7 | 7 | 7 | 140452 | cargo selection protein (mannose 6 phosphate receptor binding protein) |
| GTATTGGGGC | 5 | 7 | 0 | 0 | 0 | 0 | | |
| GTCATCACCA | 35 | 22 | 0 | 0 | 0 | 0 | 107382 | KIAA1517 protein |
| GTCATCACCA | 35 | 22 | 0 | 0 | 0 | 0 | 257045 | Homo sapiens cDNA: FLJ23415 fis, clone HEP20738 |
| GTCATCACCA | 35 | 22 | 0 | 0 | 0 | 0 | 32966 | guanylate cyclase activator 2B (uroguanylin) |
| GTCATCACCA | 35 | 22 | 0 | 0 | 0 | 0 | 68877 | cytochrome b-245, alpha polypeptide |
| GTCCGAGTGC | 17 | 3 | 0 | 0 | 0 | 0 | 3337 | transmembrane 4 superfamily member 1 |
| GTCCTGAACA | 7 | 3 | 0 | 0 | 0 | 0 | 78546 | ATPase, Ca++ transporting, plasma membrane 1 |
| GTCCTGAACA | 7 | 3 | 0 | 0 | 0 | 0 | 8258 | DKFZP434D1335 protein |
| GTGCACTGAG | 118 | 48 | 14 | 7 | 12 | 13 | 181244 | major histocompatibility complex, class I, A |
| GTGCACTGAG | 118 | 45 | 14 | 7 | 12 | 13 | 277477 | major histocompatibility complex, class I, C |
| GTGCCTGAGA | 18 | 15 | 2 | 6 | 7 | 3 | 77886 | lamin A/C |
| GTGGCGGGAA | 3 | 15 | 1 | 0 | 4 | 0 | | |
| GTGGGGGCGC | 5 | 22 | 2 | 0 | 1 | 0 | 254105 | enolase 1, (alpha) |
| GTGGTGGCAG | 29 | 11 | 1 | 0 | 10 | 3 | 194691 | retinoic acid induced 3 |
| GTGGTTCACG | 4 | 5 | 0 | 0 | 0 | 0 | 272088 | ESTs, Moderately similar to |
| GTGGTTCACG | 4 | 5 | 0 | 0 | 0 | 0 | 62192 | coagulation factor III (thromboplastin, tissue factor) |
| GTGTTGGGGA | 21 | 19 | 8 | 6 | 1 | 3 | 55016 | hypothetical protein FLJ21935 |
| GTTTAGAGGG | 5 | 16 | 0 | 0 | 2 | 1 | 181874 | interferon-induced protein with tetratricopeptide repeats 4 |
| TAAATTGCAA | 103 | 59 | 8 | 17 | 5 | 3 | 56205 | Insulin induced gene 1 |
| TAAGGCCTTT | 6 | 9 | 1 | 0 | 0 | 1 | 20149 | deleted in lymphocytic leukemia, 1 |
| TAAGGCCTTT | 6 | 9 | 1 | 0 | 0 | 1 | 42945 | acid sphingomyelinase-like phosphodiesterase |
| TAATCCCAGC | 37 | 33 | 8 | 7 | 16 | 13 | | |
| TAATTTGCAT | 25 | 2 | 1 | 1 | 2 | 0 | 79368 | epithelial membrane protein 1 |
| TACGGTGTGG | 7 | 13 | 2 | 2 | 1 | 0 | 105460 | DKFZP56400823 protein |
| TACTCGGCCA | 10 | 5 | 0 | 0 | 1 | 0 | 79474 | tyrosine 3-monooxygenase/tryptophan 5-monooxygenase activation protein, epsilon polypeptide |

TABLE 6-continued

| Tag_Sequence | NC1 | NC2 | AD1 | AD2 | CA1 | CA2 | UNI ID | Description |
|---|---|---|---|---|---|---|---|---|
| TACTGTGGAT | 4 | 11 | 0 | 2 | 2 | 1 | 21537 | protein phosphatase 1, catalytic subunit, beta isoform |
| TAGACTAGCA | 31 | 27 | 6 | 6 | 22 | 4 | 100090 | tetraspan 3 |
| TAGGATGGGG | 24 | 30 | 4 | 7 | 6 | 1 | 76941 | ATPase, Na+/K+ transporting, beta 3 polypeptide |
| TATGATGAGC | 13 | 21 | 2 | 2 | 1 | 5 | 205126 | Homo sapiens cDNA: FLJ22667 fis, clone HSI08385 |
| TCACAGTGCC | 26 | 7 | 3 | 1 | 3 | 4 | 81008 | filamin B, beta (actin-binding protein-278) |
| TCACCGGTCA | 118 | 75 | 10 | 10 | 5 | 6 | 290070 | gelsolin (amyloidosis, Finnish type) |
| TCAGAGCGCT | 5 | 21 | 0 | 7 | 0 | 1 | 92323 | FXYD domain-containing ion transport regulator 3 |
| TCAGCTGCAA | 56 | 16 | 0 | 0 | 9 | 3 | 284199 | mucin 12 |
| TCAGCTGCAA | 56 | 16 | 0 | 0 | 9 | 3 | 301888 | Homo sapiens cDNA FLJ11205 fis, clone PLACE1007843 |
| TCGGAGCTGT | 21 | 20 | 9 | 6 | 3 | 0 | 4055 | G protein-coupled receptor kinase-interactor 1 |
| TCTGAATTAT | 24 | 16 | 0 | 0 | 1 | 0 | 50964 | carcinoembryonic antigen-related cell adhesion molecule 1 (biliary glycoprotein) |
| TGACTAATTG | 7 | 9 | 2 | 0 | 0 | 3 | 293380 | ESTs |
| TGAGTGACAG | 9 | 68 | 0 | 6 | 3 | 7 | 205126 | Homo sapiens cDNA: FLJ22667 fis, clone HSI08385 |
| TGAGTGACAG | 9 | 68 | 0 | 6 | 3 | 7 | 271888 | ESTs |
| TGATCTCTGT | 6 | 7 | 1 | 0 | 1 | 1 | 30738 | hypothetical protein FLJ10407 |
| TGCAGCACGA | 6 | 185 | 5 | 30 | 24 | 16 | 110309 | major histocompatibility complex, class I, F |
| TGCAGCGCCT | 16 | 9 | 1 | 1 | 1 | 1 | 77573 | uridine phosphorylase |
| TGCCGCCCGC | 14 | 5 | 2 | 2 | 1 | 0 | 202097 | procollagen C-endopeptidase enhancer |
| TGCTCCTACC | 140 | 113 | 70 | 22 | 17 | 22 | 111732 | Fc fragment of IgG binding protein |
| TGCTCCTACC | 140 | 113 | 70 | 22 | 17 | 22 | 301256 | Homo sapiens chromosome 19, cosmid R30669 |
| TGGCCATCTG | 30 | 24 | 8 | 7 | 3 | 4 | 184052 | PP1201 protein |
| TGGCGCGTGT | 25 | 8 | 0 | 0 | 9 | 5 | 25640 | claudin 3 |
| TGGCTACTTA | 6 | 9 | 1 | 0 | 1 | 2 | 117950 | multifunctional polypeptide similar to SAICAR synthetase and AIR carboxylase |
| TGGGGAGAGG | 43 | 18 | 20 | 7 | 3 | 7 | 288998 | S100-type calcium binding protein A14 |
| TTAACCCCTC | 34 | 14 | 5 | 9 | 1 | 5 | 78224 | ribonuclease, RNase A family, 1 (pancreatic) |
| TTATGGTGTG | 11 | 17 | 0 | 0 | 0 | 0 | 271499 | ESTs |
| TTCCACTAAC | 29 | 9 | 7 | 4 | 5 | 5 | 79706 | plectin 1, intermediate filament binding protein, 500 kD |
| TTCCGCGTTC | 5 | 16 | 0 | 0 | 2 | 2 | 137274 | ESTs, Weakly similar to |
| TTCTGGTGCG | 8 | 2 | 0 | 0 | 1 | 0 | 119251 | ubiquinol-cytochrome c reductase core protein 1 |
| TTCTGTAGCC | 13 | 23 | 4 | 2 | 4 | 2 | 5541 | ATPase, Ca++ transporting, ubiquitous |
| TTGGACCTGG | 33 | 31 | 7 | 18 | 12 | 16 | 89761 | ATP synthase, H+ transporting, mitochondrial F1 complex, delta subunit |
| TTGGGGTTTC | 111 | 184 | 50 | 81 | 67 | 50 | 62954 | ferritin, heavy polypeptide 1 |
| TTTAACGGCC | 93 | 67 | 36 | 35 | 11 | 30 | mito | Tag matches mitochondrial sequence |
| TTTCCTCTCA | 21 | 8 | 6 | 2 | 4 | 3 | 184510 | stratifin |
| TTTCCTCTCA | 21 | 8 | 6 | 2 | 4 | 3 | 303400 | ESTs |
| TTTCTCGTCG | 10 | 16 | 2 | 3 | 0 | 2 | 1686 | guanine nucleotide binding protein (G protein), alpha 11 (Gq class) |
| TTTGGTTTCA | 2 | 13 | 0 | 0 | 0 | 0 | | carcinoembryonic antigen-related cell adhesion molecule 1 (biliary |
| TTTTCTGCAT | 8 | 7 | 1 | 0 | 1 | 2 | 50964 | glycoprotein) |
| TTTTCTGCAT | 8 | 7 | 1 | 0 | 1 | 2 | 77318 | platelet-activating factor acetylhydrolase, isoform Ib, alpha subunit (45 kD) |
| TTTTTACTGA | 32 | 19 | 10 | 10 | 8 | 1 | 111577 | integral membrane protein 2C |

REFERENCES

1. Cancer Facts & FIGS. 1998: American Cancer Society, 1998.
2. Inger, D. B. Colorectal cancer screening, Prim Care. 26: 179-187, 1999.
3. Velculescu, V. E., Zhang, L., Vogelstein, B., and Kinzler, K. W. Serial Analysis Of Gene Expression, Science. 270: 484-487, 1995.
4. Zhang, L., Zhou, W., Velculescu, V. E., Kern, S. E., Hruban, R. H., Hamilton, S. R., Vogelstein, B., and Kinzler, K. W. Gene Expression Profiles in Normal and Cancer Cells, Science. 276: 1268-1272, 1997.
5. Lal, A., Lash, A. E., Altschul, S. F., Velculescu, V., Zhang, L., McLendon, R. E., Marra, M. A., Prange, C., Morin, P. J., Polyak, K., Papadopoulos, N., Vogelstein, B., Kinzler, K. W., Strausberg, R. L., and Riggins, G. J. A public database for gene expression in human cancers, Cancer Res. 59: 5403-5407, 1999.
6. St Croix, B., Rago, C., Velculescu, V., Traverso, G., Romans, K. E., Montgomery, E., Lal, A., Riggins, G. J., Lengauer, C., Vogelstein, B., and Kinzler, K. W. Genes expressed in human tumor endothelium, Science. 289: 1197-1202, 2000.
7. Guy-Crotte, O., Amouric, M., and Figarella, C. Characterization and N-terminal sequence of a degradation product of 14,000 molecular weight isolated from human pancreatic juice, Biochem Biophys Res Commun. 125: 516-523, 1984.
8. Terazono, K., Yamamoto, H., Takasawa, S., Shiga, K., Yonemura, Y., Tochino, Y., and Okamoto, H. A novel gene activated in regenerating islets, J Biol Chem. 263: 2111-2114, 1988.
9. Watanabe, T., Yonekura, H., Terazono, K., Yamamoto, H., and Okamoto, H. Complete nucleotide sequence of human reg gene and its expression in normal and tumoral tissues. The reg protein, pancreatic stone protein, and pancreatic thread protein are one and the same product of the gene, J Biol Chem. 265: 7432-7439, 1990.
10. Rechreche, H., Montalto, G., Mallo, G. V., Vasseur, S., Marasa, L., Soubeyran, P., Dagorn, J. C., and Iovanna, J. L. pap, reg Ialpha and reg Ibeta mRNAs are concomitantly up-regulated during human colorectal carcinogenesis, Int J Cancer. 81: 688-694, 1999.
11. Skonier, J., Neubauer, M., Madisen, L., Bennett, K., Plowman, G. D., and Purchio, A. F. cDNA cloning and sequence analysis of beta ig-h3, a novel gene induced in a human adenocarcinoma cell line after treatment with transforming growth factor-beta, DNA Cell Biol. 11: 511-522, 1992.
12. Escribano, J., Hernando, N., Ghosh, S., Crabb, J., and Coca-Prados, M. cDNA from human ocular ciliary epithelium homologous to beta ig-h3 is preferentially expressed as an extracellular protein in the corneal epithelium, J Cell Physiol. 160: 511-521, 1994.
13. Munier, F. L., Korvatska, E., Djemai, A., Le Paslier, D., Zografos, L., Pescia, G., and Schorderet, D. F. Kerato- 14. Fleming, A. On a remarkable bacteriolytic element found in tissues and secretions, Proceedings of the Royal Society. 93: 306-317, 1922.
15. Sugi, K., Saitoh, O., Hirata, I., and Katsu, K. Fecal lactoferrin as a marker for disease activity in inflammatory bowel disease: comparison with other neutrophil-derived proteins, Am J Gastroenterol. 91: 927-934, 1996.
16. van der Sluys Veer, A., Brouwer, J., Biemond, I., Bohbouth, G. E., Verspaget, H. W., and Lamers, C. B. Fecal lysozyme in assessment of disease activity in inflammatory bowel disease, Dig Dis Sci. 43: 590-595, 1998.
17. Tomita, H., Sato, S., Matsuda, R., Sugiura, Y., Kawaguchi, H., Niimi, T., Yoshida, S., and Morishita, M. Serum lysozyme levels and clinical features of sarcoidosis, Lung. 177: 161-167, 1999.
18. Ho, S. B., Itzkowitz, S. H., Friera, A. M., Jiang, S. H., and Kim, Y. S. Cell lineage markers in premalignant and malignant colonic mucosa, Gastroenterology. 97: 392404, 1989.
19. Yamada, R. and Kera, Y. D-amino acid hydrolysing enzymes, Exs. 85: 145-155, 1998.
20. Bootcov, M. R., Bauskin, A. R., Valenzuela, S. M., Moore, A. G., Bansal, M., He, X. Y., Zhang, H. P., Donnellan, M., Mahler, S., Pryor, K., Walsh, B. J., Nicholson, R. C., Fairlie, W. D., Por, S. B., Robbins, J. M., and Breit, S. N. MIC-1, a novel macrophage inhibitory cytokine, is a divergent member of the TGF-beta superfamily, Proc Natl Acad Sci U S A. 94: 11514-11519, 1997.
21. Paralkar, V. M., Vail, A. L., Grasser, W. A., Brown, T. A., Xu, H., Vukicevic, S., Ke, H. Z., Qi, H., Owen, T. A., and Thompson, D. D. Cloning and characterization of a novel member of the transforming growth factor-beta/bone morphogenetic protein family, J Biol Chem. 273: 13760-13767, 1998.
22. Notterman, D. A., Alon, U., Sierk, A. J., Levine, A. J., Transcriptional Gene Expression Profiles of Colorectal Adenoma, Adenocarcinoma, and Normal Tissue Examined by Oligonucleotide Arrays, Cancer Res. 61: 3124-3130, 2001.
23. Zhou, W., Sokoll, L. J., Brusek, D. J., Zhang, L., Velculsescu, V., Goldin, S. B., Hruban, R. H., Kem, S. E., Hamilton, S. R., Chan, D. W., Vogelstein, B., and Kinzier, K. W. Identifying markers for pancreatic cancer by gene expression analysis, Can Epid Bio & Prev. 7. 109-112, 1998.
24. Brown, D. A., Liu, T., Ward, R. L., Hawkins, N. J., Fairlie, W. D., Bauskin, A. R., Russell, P. J., Quinn, D. I., Grygiel, J. J., Moore, A. G., Sutherland, R. L., Turner, J., Kingsley, E. A., and Breit, S. N. Macrophage Inhibitory Cytokine-1 (MIC-1) in epithelial neoplasia, Submitted., 2001.

We claim:

1. A method for detection of colorectal cancer, comprising the steps of:
    detecting renal dipeptidase in blood of a subject; and
    comparing the amount of renal dipeptidase in blood of the subject to the amount of renal dipeptidase in normal subjects;
    detecting an elevated amount of renal dipeptidase in the blood of the subject which is an indicator of colorectal cancer in the subject.

2. A method for detection of colorectal cancer, comprising the steps of:
    detecting renal dipeptidase in feces of a subject; and
    comparing the amount of renal dipeptidase in feces of the subject to the amount of renal dipeptidase in normal subjects;
    detecting an elevated amount of renal dipeptidase in the feces of the subject which is an indicator of colorectal cancer in the subject.

3. The method of claim 1 further comprising: determining if the renal dipeptidase detected in the blood comprises a tumor-specific glycoform of renal dipeptidase.

4. The method of claim 2 further comprising: determining if the renal dipeptidase detected in the feces comprises a tumor-specific glycoform of renal dipeptidase.

5. The method of claim 1 further comprising: determining if the renal dipeptidase detected in the blood binds to L lectin from *Phaseolus vulgaris* hemagglutinin.

6. The method of claim 2 further comprising: determining if the renal dipeptidase detected in the feces binds to L lectin from *Phaseolus vulgaris* hemagglutinin.

7. The method of claim 1 further comprising: determining if the renal dipeptidase detected in the blood binds to L lectin from *Sambucus nigra* hemagglutinin.

8. The method of claim 2 further comprising:
    determining if the renal dipeptidase detected in the feces binds to L lectin from *Sambucus nigra* hemagglutinin.

9. The method of claim 1 wherein the normal subjects are tumor free.

10. The method of claim 1 wherein the normal subjects are tumor free as determined by colonoscopy.

11. The method of claim 1 further comprising:
    indicating that the subject has a marker for colorectal cancer.

12. The method of claim 2 wherein the normal subjects are tumor free.

13. The method of claim 2 wherein the normal subjects are tumor free as determined by colonoscopy.

14. The method of claim 2 further comprising:
    indicating that the subject has a marker for colorectal cancer.

15. The method of claim 1 wherein the subject is presymptomatic.

16. The method of claim 2 wherein the subject is presymptomatic.

17. The method of claim 1 wherein the subject has metastatic colon cancer.

18. The method of claim 2 wherein the subject has metastatic colon cancer.

* * * * *

UNITED STATES PATENT AND TRADEMARK OFFICE
CERTIFICATE OF CORRECTION

PATENT NO. : 8,029,764 B2  Page 1 of 1
APPLICATION NO. : 10/487934
DATED : October 4, 2011
INVENTOR(S) : Phillip Buckhaults et al.

It is certified that error appears in the above-identified patent and that said Letters Patent is hereby corrected as shown below:

Title page, PCT Pub. Date:
Please delete "May 3, 2003" and insert -- March 20, 2003 --

Signed and Sealed this
Twelfth Day of June, 2012

David J. Kappos
*Director of the United States Patent and Trademark Office*